US012796940B2

(12) United States Patent
Landgraf et al.

(10) Patent No.: US 12,796,940 B2
(45) Date of Patent: Nov. 17, 2026

(54) METHODS AND SYSTEMS FOR DETERMINING A PHYSIOLOGICAL OR BIOLOGICAL STATE OR CONDITION OF A SUBJECT

(71) Applicant: Eko Health, Inc., Emeryville, CA (US)

(72) Inventors: Connor Landgraf, Oakland, CA (US); John Maidens, Oakland, CA (US); Subramaniam Venkatraman, Oakland, CA (US); Avi Shapiro, Oakland, CA (US); Steve L. Pham, Oakland, CA (US)

(73) Assignee: EKO HEALTH, INC., Emeryville, CA (US)

( * ) Notice: Subject to any disclaimer, the term of this patent is extended or adjusted under 35 U.S.C. 154(b) by 798 days.

(21) Appl. No.: 17/269,974

(22) PCT Filed: Aug. 20, 2019

(86) PCT No.: PCT/US2019/047333
§ 371 (c)(1),
(2) Date: Feb. 19, 2021

(87) PCT Pub. No.: WO2020/041363
PCT Pub. Date: Feb. 27, 2020

(65) Prior Publication Data

US 2021/0345934 A1 Nov. 11, 2021

Related U.S. Application Data

(60) Provisional application No. 62/720,796, filed on Aug. 21, 2018, provisional application No. 62/879,317, filed on Jul. 26, 2019.

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/0006* (2013.01); *A61B 5/0022* (2013.01);
(Continued)

(58) Field of Classification Search
CPC ..... A61B 5/349; A61B 5/0006; A61B 5/0022; A61B 5/0205; A61B 5/029; A61B 5/6898
See application file for complete search history.

(56) References Cited

U.S. PATENT DOCUMENTS 9,492,138 B2 * 11/2016 Kapoor .................. A61B 5/742
9,736,625 B1 * 8/2017 Landgraf ................ H04W 4/70
(Continued)

FOREIGN PATENT DOCUMENTS

CN 107960990 A * 4/2018 ............... A61B 5/00
JP 2018503885 A 2/2018
(Continued)

OTHER PUBLICATIONS

Ejection Fraction (Year: 2022).*
(Continued)

*Primary Examiner* — Amanda L Steinberg
*Assistant Examiner* — Laura Hodge
(74) *Attorney, Agent, or Firm* — McCoy Russell LLP

(57) ABSTRACT

The present disclosure provides methods, devices, and systems for determining a state or condition of a subject. A method for determining a state or condition of a heart of a subject may include using a monitoring device comprising an electrocardiogram (ECG) sensor and an audio sensor to measure ECG data and audio data from an organ of the subject, and transmitting the ECG data and the audio data wirelessly to a computing device. A trained algorithm may be used to process the ECG data and the audio data to determine the state or condition of the organ of the subject. More specifically, the trained algorithm can be customized
(Continued)

for a specific indication or condition. An output indicative of the state or condition of the heart of the subject may be provided on the computing device.

5 Claims, 21 Drawing Sheets

(51) Int. Cl.

*A61B 5/029* (2006.01)
*A61B 5/33* (2021.01)
*A61B 5/339* (2021.01)
*A61B 7/00* (2006.01)

(52) U.S. Cl.

CPC ................ *A61B 5/029* (2013.01); *A61B 5/33* (2021.01); *A61B 5/339* (2021.01); *A61B 5/6898* (2013.01); *A61B 7/00* (2013.01); *A61B 7/003* (2013.01)

(56) References Cited

U.S. PATENT DOCUMENTS

| | | | | | |
|---|---|---|---|---|---|
| 2005/0130321 | A1 | 6/2005 | Nicholson et al. | | |
| 2006/0106322 | A1 | 5/2006 | Arand et al. | | |
| 2007/0276270 | A1* | 11/2007 | Tran | A61B 5/0022 | 600/508 |
| 2011/0137193 | A1* | 6/2011 | Ghanem | G16H 40/63 | 600/515 |
| 2012/0203076 | A1* | 8/2012 | Fatta | A61B 5/681 | 600/300 |
| 2012/0296228 | A1* | 11/2012 | Zhang | A61B 5/4848 | 600/513 |
| 2012/0310115 | A1* | 12/2012 | Bedingham | A61B 7/04 | 600/586 |
| 2013/0172691 | A1 | 7/2013 | Tran | | |
| 2013/0289424 | A1* | 10/2013 | Brockway | A61B 5/6801 | 600/509 |
| 2015/0005588 | A1 | 1/2015 | Herken et al. | | |
| 2015/0164349 | A1* | 6/2015 | Gopalakrishnan | A61B 5/746 | 600/508 |
| 2015/0250396 | A1 | 9/2015 | Ahmed et al. | | |
| 2016/0120416 | A1* | 5/2016 | Kim | A61B 7/023 | 600/528 |
| 2016/0228072 | A1 | 8/2016 | Zhang et al. | | |
| 2016/0270738 | A1* | 9/2016 | Volpe | A61B 5/25 | |
| 2017/0238812 | A1 | 8/2017 | Atlas | | |
| 2018/0028144 | A1* | 2/2018 | Chen | A61B 5/316 | |
| 2018/0116626 | A1 | 5/2018 | Darbari et al. | | |
| 2018/0168473 | A1 | 6/2018 | Du et al. | | |
| 2019/0059748 | A1* | 2/2019 | Kaiser | A61B 7/026 | |

FOREIGN PATENT DOCUMENTS

| | | | | | |
|---|---|---|---|---|---|
| WO | WO-2010083526 | A2 * | 7/2010 | A61B 5/02 |
| WO | WO-2013184315 | A1 * | 12/2013 | A61B 5/0006 |
| WO | 2016077786 | A1 | 5/2016 | |
| WO | 2017215278 | A1 | 12/2017 | |
| WO | 2018118935 | A1 | 6/2018 | |
| WO | 2019070978 | A1 | 4/2019 | |

OTHER PUBLICATIONS

Japanese Patent Office, Office Action Issued in Application No. 2021-533378, Jan. 24, 2023, 6 pages.
European Patent Office, Office Action Issued in Application No. 19851381.4, Aug. 23, 2022, Netherlands, 6 pages.
ISA United States Patent and Trademark Office, International Search Report Issued in Application No. PCT/US2019/047333, Dec. 6, 2019, WIPO, 4 pages.
ISA United States Patent and Trademark Office, Written Opinion of the International Searching Authority Issued in Application No. PCT/US2019/047333, Dec. 6, 2019, WIPO, 20 pages.
Phanphaisarn, W. et al., "Heart detection and diagnosis based on ECG and EPCG relationships," Medical Devices, vol. 4, Aug. 25, 2011, 12 pages.
Verma, D., "CPS—Heart: Cyber-Physical Systems for Cardiovascular Diseases," Proceedings of the Workshop Proceedings of the 19th International Conference on Distributed Computing and Networking, Jan. 4, 2018, Varanasi, India, 5 pages.
European Patent Office, Extended European Search Report Issued in Application No. 19851381.4, Apr. 21, 2022, Germany, 22 pages.

* cited by examiner

910

| | | Gold Standard Murmur | No Murmur | | |
|---|---|---|---|---|---|
| Algorithm | Murmur | 349 | 1 | 1.00 | Positive predictive value |
| | No Murmur | 35 | 121 | 0.78 | Negative predictive value |
| | | 0.91 | 0.99 | 0.95 | |
| | 95% CI lower | 0.88 | 0.96 | 0.90 | |
| | 95% CI upper | 0.93 | 1.00 | 0.95 | |
| | | Sensitivity | Specificity | Accuracy | |

920

Sensitivity breakdown by intensity

| | | All heart murmurs Grade 1-1.5 | Grade 2-2.5 | Grade 3-3.5 | Grade >=4 |
|---|---|---|---|---|---|
| Algorithm | Murmur | 52 | 160 | 58 | 39 |
| | No Murmur | 18 | 7 | 0 | 0 |
| | Sensitivity | 0.65 | 0.96 | 1.00 | 1.00 |
| | 95% CI lower | 0.54 | 0.92 | 0.96 | 0.91 |
| | 95% CI upper | 0.75 | 0.98 | 1.00 | 1.00 |

930

| | | Echo-confirmed pathologic murmurs Grade 1-1.5 | Grade 2-2.5 | Grade 3-3.5 | Grade >=4 |
|---|---|---|---|---|---|
| Algorithm | Murmur | 15 | 136 | 98 | 39 |
| | No Murmur | 13 | 6 | 0 | 0 |
| | Sensitivity | 0.66 | 0.96 | 1.00 | 1.00 |
| | 95% CI lower | 0.50 | 0.91 | 0.96 | 0.91 |
| | 95% CI upper | 0.79 | 0.98 | 1.00 | 1.00 |

FIG. 9

Sensitivity breakdown by pathology

Gold Standard

| Algorithm | AR | AS | ASD | AVSurg | AVVR |
|---|---|---|---|---|---|
| Murmur | 4 | 67 | 10 | 5 | 5 |
| No Murmur | 4 | 1 | 1 | 2 | 2 |
| Sensitivity | 0.50 | 0.99 | 0.91 | 0.71 | 0.71 |
| 95% CI lower | 0.22 | 0.92 | 0.62 | 0.56 | 0.56 |
| 95% CI upper | 0.78 | 1.00 | 0.98 | 0.92 | 0.92 |

| | BAY | Coarc | HOCM | MR | PDA |
|---|---|---|---|---|---|
| Murmur | 9 | 5 | 3 | 18 | 7 |
| No Murmur | 0 | 1 | 1 | 5 | 0 |
| Sensitivity | 1.00 | 0.83 | 0.75 | 0.78 | 1.00 |
| 95% CI lower | 0.70 | 0.44 | 0.30 | 0.58 | 0.65 |
| 95% CI upper | 1.00 | 0.97 | 0.95 | 0.90 | 1.00 |

| | PR | PS | RV-PAconduit | SubAS | SupraPS |
|---|---|---|---|---|---|
| Murmur | 2 | 34 | 11 | 20 | 5 |
| No Murmur | 0 | 1 | 0 | 0 | 0 |
| Sensitivity | 1.00 | 0.97 | 1.00 | 1.00 | 1.00 |
| 95% CI lower | 0.34 | 0.85 | 0.74 | 0.84 | 0.57 |
| 95% CI upper | 1.00 | 0.99 | 1.00 | 1.00 | 1.00 |

| | TF | TFsurg | VSD | Other |
|---|---|---|---|---|
| Murmur | 10 | 12 | 47 | 20 |
| No Murmur | 0 | 0 | 1 | 0 |
| Sensitivity | 1.00 | 1.00 | 0.98 | 1.00 |
| 95% CI lower | 0.72 | 0.76 | 0.59 | 0.84 |
| 95% CI upper | 1.00 | 1.00 | 1.00 | 1.00 |

FIG. 10

(1) Data transfer from hardware to mobile device over BLE
(2) .WAV file uploaded from mobile device to EkoCloud
(3) Data sent for analysis using the EAS API
(4) Analysis result returned as JSON file
(5) Analysis result sent to mobile device and displayed in Mobile App Tom Hill No Murmur Normal Sinus Rhythm

| | |
|---|---|
| Heart Rate | 62 *BPM* |
| QRS Duration | 85 *ms* |
| Normalized EMAT | 10 % |

These results are not a diagnosis, only a possible finding.

| | |
|---|---|
| Position | LUSB |

METHODS AND SYSTEMS FOR DETERMINING A PHYSIOLOGICAL OR BIOLOGICAL STATE OR CONDITION OF A SUBJECT

CROSS-REFERENCE

This application is a U.S. National Phase of International Patent Application No. PCT/US2019/047333, entitled "METHODS AND SYSTEMS FOR DETERMINING A PHYSIOLOGICAL OR BIOLOGICAL STATE OR CONDITION OF A SUBJECT," filed on Aug. 20, 2019, which claims the benefit of U.S. Provisional Patent Application No. 62/720,796, filed Aug. 21, 2018, and U.S. Provisional Patent Application No. 62/879,317, filed on Jul. 26, 2019, each of which is entirely incorporated herein by reference.

BACKGROUND

As healthcare costs continue to escalate, solutions to reduce the cost and improve the efficacy of diagnostic efforts may become increasingly important. In other situations, improving access to medical diagnostic and monitoring capabilities may be desirable. These objectives may be particularly valuable for cardiac care, since cardiac function is vital to human health and well-being, and cardiovascular diseases (CVDs) continue to be the most common cause of death. Such cardiovascular diseases may include coronary artery diseases (CAD), such as angina and myocardial infarction (or a heart attack). Other CVDs may include stroke, heart failure, hypertensive heart disease, rheumatic heart disease, cardiomyopathy, heart arrhythmia, congenital heart disease, valvular heart disease, carditis, aortic aneurysms, peripheral artery disease, thromboembolic disease, and venous thrombosis.

However, traditional cardiac monitoring and evaluation tools may not be well-suited to non-clinical environments. Equipment may be costly and difficult to use for untrained lay users. Cardiac monitoring equipment may involve numerous sensors, requiring specific placement, which may be difficult and time consuming for lay users to apply, and may be difficult for a user to apply to themselves—thereby preventing or discouraging regular use. Sensor cables can become tangled, pulled, and damaged, further frustrating users and reducing equipment reliability. In addition, currently available cardiac monitors may provide continuous monitoring over a short period of time, such as 2 weeks or 30 days. This time limitation may be significant because cardiac conditions may manifest themselves over a long period of months or years, where a short continuous monitoring window may not be useful for the lifetime of the disease.

SUMMARY

The present disclosure provides methods and systems for determining a state or condition of a subject, such as a body part of the subject. Methods and systems of the present disclosure may be used to monitor a state or condition of an organ (e.g., a heart, lung, or bowel) or organ system (e.g., cardiovascular, pulmonary, gastrointestinal, or circulatory) of the subject, over various time periods. This may advantageously permit the subject to be monitored for a health or disease condition over a longer period of time.

An aspect of the present disclosure provides a method for determining a state or condition of a heart of a subject. The method may comprise (a) using a monitoring device comprising an electrocardiogram (ECG) sensor to measure electrocardiogram (ECG) data and an audio sensor to measure audio data from the heart of the subject; (b) transmitting the ECG data and the audio data wirelessly to a computing device; (c) using a trained algorithm to process the ECG data and the audio data to determine the state or condition of the heart of the subject; and (d) providing an output indicative of the state or condition of the heart of the subject on the computing device.

In some embodiments, the monitoring device is mobile. In some embodiments, the computing device is mobile. In some embodiments, in (b), the ECG data and the audio data are transmitted in a common packet. In some embodiments, providing the output indicative of the state or condition of the heart of the subject comprises a determining a presence or absence of a low ejection fraction of a left ventricle of the heart of the subject. In some embodiments, the ECG data comprises single lead ECG data. In some embodiments, the ECG data comprises three lead ECG data. In some embodiments, the ECG data comprises twelve lead ECG data. In some embodiments, the ECG data comprises chest cavity, lung, or intra-thoracic impedance measurement data.

In some embodiments, in (c), the ECG data and the audio data are processed by one or more computer processors of the computing device. In some embodiments, the method further comprises processing the ECG data and the audio data in a distributed computing system. In some embodiments, in (c), the ECG data and the audio data are processed in a distributed computing system. In some embodiments, the trained algorithm is a neural network. In some embodiments, the state or condition of the heart of the subject is determined at an accuracy of at least about 90% for independent subjects. In some embodiments, the accuracy is at least about 95%. In some embodiments, the state or condition of the heart of the subject is determined to be a no-failure state or condition at a specificity of at least about 90% for independent subjects. In some embodiments, the specificity is at least about 95%. In some embodiments, the state or condition of the heart of the subject is correlated with a magnitude and a duration of the audio data within a frequency band of the audio data. In some embodiments, the output is an alert indicative of an adverse state or condition of the heart.

In some embodiments, (a)-(d) are performed in a time period that is less than or equal to 1 minute. In some embodiments, the computing device is within about 30 feet of the monitoring device. In some embodiments, the computing device is within about 10 feet of the monitoring device. In some embodiments, the computing device is within about 5 feet of the monitoring device.

In some embodiments, the state or condition of a heart is a valve disease. In some embodiments, the state or condition of a heart is an arrythmia. In some embodiments, the state or condition of a heart is a heart failure. In some embodiments, the state or condition of a heart is congenital heart disease.

In another aspect, the present disclosure provides a method for determining a state or condition of a heart of a subject. The method may comprise (a) using a monitoring device comprising an ECG sensor and an audio sensor to measure ECG data and audio data from the heart of the subject over a time period; (b) transmitting the ECG data and the audio data to a computing device comprising a user interface; and (c) presenting the ECG data and the audio data on the user interface over the time period in substantially real time. In some embodiments, the monitoring device is mobile. In some embodiments, the computing device is mobile. In some embodiments, the user interface comprises a web-based user interface. In some embodiments, the web-based user interface comprises a secure web browser.

In some embodiments, the monitoring device is mobile. In some embodiments, the monitoring device is a mobile device. In some embodiments, the computing device is mobile. In some embodiments, the computing device is a mobile device. In some embodiments, the computing device is part of a cloud system. In some embodiments, the user interface comprises a web-based user interface. In some embodiments, the web-based user interface comprises a secure web browser.

In some embodiments, the method further comprises, prior to (b), using the ECG data and the audio data to generate a common packet structure. In some embodiments, the method further comprises inserting a rolling packet sequence into the common packet structure. In some embodiments, further comprises: (i) receiving at the computing device a sequential data packet having a non-sequential rolling packet sequence, and (ii) displaying a warning on a user interface of the computing device, which warning is indicative of a compromise in a link between the monitoring device and the computing device.

In some embodiments, the ECG data and the audio data are transmitted from the monitoring device to the computing device via a radio frequency communication. In some embodiments, the method further comprises storing the ECG data and the audio data locally on the monitoring device. In some embodiments, (a)-(c) are performed in a time period that is less than or equal to 1 minute. In some embodiments, the computing device is within about 30 feet of the monitoring device. In some embodiments, the computing device is within about 10 feet of the monitoring device. In some embodiments, the computing device is within about 5 feet of the monitoring device.

In some embodiments, the state or condition of a heart is a valve disease. In some embodiments, the state or condition of a heart is an arrythmia. In some embodiments, the state or condition of a heart is a heart failure. In some embodiments, the state or condition of a heart is congenital heart disease.

In another aspect, the present disclosure provides a method for determining a state or condition of a heart of a subject. The method may comprise (a) using a monitoring device comprising an ECG sensor and an audio sensor to measure a first set of ECG data and audio data from the heart of the subject over a first time period; (b) transmitting the first set of ECG data and audio data to a computing device; (c) using the monitoring device to measure a second set of ECG data and audio data from the heart of the subject over a second time period, wherein the second time period is different from the first time period; (d) transmitting the second set of ECG data and audio data to the computing device; (e) processing at least the first set of ECG data and audio data and the second set of ECG data and the audio data to provide an output indicative of the state or condition of the heart of the subject on the computing device over at least the first time period and the second time period.

In some embodiments, the method further comprises using the monitoring device to measure at least a third set of ECG data and audio data from the heart of the subject over one or more additional time periods. In some embodiments, the monitoring device is mobile. In some embodiments, the computing device is a mobile. In some embodiments, the state or condition of the heart of the subject comprises a risk of congestive heart failure. In some embodiments, the method further comprises automatically initiating measurement of the first or second set of ECG data and audio data when a threshold signal quality level is detected. In some embodiments, the second set of ECG data and audio data is processed by one or more computer processors of the computing device. In some embodiments, the second set of ECG data and audio data is processed in a distributed computing system. In some embodiments, (a)-(e) are performed in a time period that is less than or equal to 1 minute. In some embodiments, the computing device is within about 30 feet of the monitoring device. In some embodiments, the computing device is within about 10 feet of the monitoring device. In some embodiments, the computing device is within about 5 feet of the monitoring device.

In some embodiments, the state or condition of a heart is a valve disease. In some embodiments, the state or condition of a heart is an arrythmia. In some embodiments, the state or condition of a heart is a heart failure. In some embodiments, the state or condition of a heart is congenital heart disease.

In another aspect, the present disclosure provides a method for determining a state or condition of a subject. The method comprises: (a) using a monitoring device external to a skin of the subject comprising an ECG sensor and/or an audio sensor to measure ECG data and/or audio data from the subject; (b) transmitting the ECG data and/or the audio data to a computing device comprising a user interface; and (c) using a trained algorithm to process the ECG data and/or the audio data to determine the state or condition of the subject; and (d) using a trained algorithm to process the ECG data (e.g., impedance data) and/or the audio data to determine the state or condition of the subject; and (e) providing an output indicative of the state or condition of the subject on the user interface.

In some embodiments, the state or condition of the subject comprises a state or condition of a heart of the subject. In some embodiments, the state or condition of the heart of the subject comprises a heart disease, disorder, or other condition, such as low ejection fraction, congestive heart failure, heart murmur (e.g., systolic murmur (such as aortic stenosis, pulmonic stenosis, mitral regurgitation, tricuspid regurgitation, or mitral valve prolapse) or diastolic murmur (such as aortic regurgitation, pulmonic regurgitation, mitral stenosis, or tricuspid stenosis)), valve disease, arrhythmia (e.g., bradycardia, tachycardia, ventricular tachycardia, ventricular fibrillation, premature ventricular contractions, supraventricular arrhythmia, superventricular tachycardia (SVT), paroxysmal superventricular tachycardia (PSVT), atrial fibrillation, Wolff-Parkinson-White Syndrome, atrial flutter, premature supraventricular contractions or premature atrial contractions (PACs), postural orthostatic tachycardia syndrome (POTS)), congenital heart disease, heart blockage, ischemia, infarction, pericarditis, hypertrophy, QT prolongation, or a combination thereof, of the subject. In some embodiments, the state or condition of the heart of the subject comprises a valve disease of the subject. In some embodiments, the state or condition of the heart of the subject comprises an arrhythmia (e.g., bradycardia, tachycardia, ventricular tachycardia, ventricular fibrillation, premature ventricular contractions, supraventricular arrhythmia, superventricular tachycardia (SVT), paroxysmal superventricular tachycardia (PSVT), atrial fibrillation, Wolff-Parkinson-White Syndrome, atrial flutter, premature supraventricular contractions or premature atrial contractions (PACs), postural orthostatic tachycardia syndrome (POTS)) of the subject. In some embodiments, the state or condition of the heart of the subject comprises a congenital heart disease of the subject. In some embodiments, the state or condition of the heart of the subject comprises a QT prolongation of the subject (e.g., which may correlate with cardiac death). In some embodiments, the ECG data comprises a QT interval, which may be indicative of a QT prolongation of the subject. In some embodiments, the audio data comprises heart audio data. In some embodiments, the output comprises a heart function parameter based on the audio data and/or the ECG data. In some embodiments, the output comprises a measure of coupling between electrical activity (ECG) and mechanical activity (heart sounds) which indicates intra-cardiac pressures or filling pressures, In some embodiments, the output comprises a measure of the time interval between the Q wave of the ECG and the S1 heart sounds (the electro-mechanical activation time).

In some embodiments, the state or condition of the subject comprises a state or condition of a lung of the subject. In some embodiments, the state or condition of the lung of the subject comprises pneumonia. In some embodiments, the data comprises lung audio data. In some embodiments, the ECG data comprises chest cavity or intra-thoracic impedance data. In some embodiments, the output comprises a lung function parameter based on the audio data and the ECG data.

In some embodiments, the state or condition of the subject comprises a state or condition of a lung of the subject. In some embodiments, the state or condition of the lung of the subject comprises a lung disease, disorder, or other condition, such as pneumonia, plural effusion, pulmonary embolism, poor airflow, chronic obstructive pulmonary disease (COPD), asthma, or a combination thereof, of the subject. In some embodiments, the state or condition of the lung of the subject comprises COPD of the subject. In some embodiments, the state or condition of the lung of the subject comprises asthma of the subject. In some embodiments, the state or condition of the lung of the subject comprises pneumonia of the subject. In some embodiments, the audio data comprises lung audio data. In some embodiments, the ECG data comprises chest cavity or intra-thoracic impedance data. In some embodiments, the output comprises a lung function parameter based on the audio data and/or the ECG data. In some embodiments the audio data from the lungs is used to calculate a lung resonance frequency, In some embodiments, a sound wave is inputted into the lungs and a responding sound is analyzed. In some embodiments, audio is captured from the lungs of the COPD patient and a resonance analysis is conducted to calculate the amount of trapped air in a COPD patient's lungs.

In some embodiments, the monitoring device is mobile. In some embodiments, the monitoring device is a mobile device. In some embodiments, the computing device is mobile. In some embodiments, the computing device is a mobile device. In some embodiments, the state or condition of the subject comprises a state or condition of a condition of a bowel of a subject.

In some embodiments, the audio data comprises bowel sounds. In some embodiments, (a)-(e) are performed in a time period that is less than or equal to 1 minute. In some embodiments, the computing device is within about 30 feet of the monitoring device. In some embodiments, the computing device is within about 10 feet of the monitoring device. In some embodiments, the computing device is within about 5 feet of the monitoring device.

In some embodiments, the state or condition of a heart is a valve disease. In some embodiments, the state or condition of a heart is an arrythmia. In some embodiments, the state or condition of a heart is a heart failure. In some embodiments, the state or condition of a heart is congenital heart disease.

In some embodiments, the state or condition of the subject comprises a state or condition of a condition of a bowel of a subject. In some embodiments, the state or condition of the bowel of the subject comprises a bowel disease, disorder, or other condition, such as inflammatory bowel disease (IBD), intestinal obstruction, hernia, infection within the digestive tract, or a combination thereof, of the subject. In some embodiments, the audio data comprises bowel audio data. In some embodiments, the output comprises a bowel function parameter based on the audio data and/or the ECG data.

In some embodiments, the state or condition of the subject comprises a state or condition of a vein of the subject. In some embodiments, the state or condition of the subject comprises a state or condition of a fistula of the subject. In some embodiments, the state or condition of the fistula of the subject comprises a state or condition of a diabetic fistula of the subject. In some embodiments, the sounds of the fistula are interpreted to create a measure of venous flow.

Another aspect of the present disclosure provides a method for determining a state or condition of a subject, comprising: using a monitoring device external to a skin of the subject comprising an electrocardiogram (ECG) sensor and an audio sensor to measure ECG data and audio data from the subject; transmitting the ECG data and the audio data to a computing device comprising a user interface; using a trained algorithm to process the ECG data and the audio data to determine the state or condition of the subject; and providing an output indicative of the state or condition of the subject on the user interface.

In some embodiments, the state or condition of the subject comprises a state or condition of a lung of the subject. In some embodiments, the state or condition of the lung of the subject comprises pneumonia. In some embodiments, the audio data comprises lung audio data. In some embodiments, the ECG data comprises chest cavity or intra-thoracic impedance data. In some embodiments, the output comprises a lung function parameter based on the audio data and the ECG data. In some embodiments, the state or condition of the subject comprises a state or condition of a bowel of a subject.

In some embodiments, the monitoring device is mobile. In some embodiments, the computing device is mobile. In some embodiments, (a)-(d) are performed in a time period that is less than or equal to 1 minute. In some embodiments, the computing device is within about 30 feet of the monitoring device. In some embodiments, the computing device is within about 10 feet of the monitoring device. In some embodiments, the computing device is within about 5 feet of the monitoring device.

In some embodiments, the state or condition of a heart is a valve disease. In some embodiments, the state or condition of a heart is an arrythmia. In some embodiments, the state or condition of a heart is a heart failure. In some embodiments, the state or condition of a heart is congenital heart disease.

Another aspect of the present disclosure presents a method for determining a state or condition of a subject, comprising: using a monitoring device comprising an electrocardiogram (ECG) sensor and an audio sensor to measure ECG data and audio data from the subject; wirelessly transmitting the ECG data and the audio data to a computing device; removing noise from the audio data to yield processed audio data; processing the ECG data and the processed audio data to determine the state or condition of the subject; and outputting the state or condition of the subject.

In some embodiments, the state or condition of the subject comprises a state or condition of an organ or body part of the subject. In some embodiments, the state or condition of the subject comprises a state or condition of a heart, lung, or bowel of the subject. In some embodiments, the noise is caused by a movement of the subject.

In some embodiments, the noise is caused by a movement of the monitoring device. In some embodiments, the state or condition of an organ or body part is a valve disease. In some embodiments, the state or condition of an organ or body part is an arrythmia. In some embodiments, the state or condition of an organ or body part is a heart failure. In some embodiments, the state or condition of an organ or body part is congenital heart disease.

In some embodiments, the state or condition of an organ or body part is chronic obstructive pulmonary disease (COPD). In some embodiments, the state or condition of an organ or body part is asthma. In some embodiments, the state or condition of an organ or body part is pneumonia. In some embodiments, the state or condition of an organ or body part is fistula. In some embodiments, the state or condition of an organ or body part is inflammatory bowel disease (IBD).

Another aspect of the present disclosure presents a method for determining a state or condition of a heart of a subject, comprising: using a monitoring device comprising an electrocardiogram (ECG) sensor and an audio sensor to generate a set of ECG data and audio data; using a trained algorithm to process a first set of features of the set of ECG data and audio data to determine the state or condition of the subject; accessing a database to identify one or more other states or conditions that are associated with a second set of features overlapping with the first set of features; and providing an output indicative of the state or condition and the one or more other states or conditions.

In some embodiments, the first set of features comprises one or more members selected from the group consisting of an intensity of audio frequency data, a pitch of the audio frequency data, a shape of the audio frequency data, a location at which the audio data is most intensely detected, and a tonal quality. In some embodiments, the first set of features comprises an average number of PR segments, ST segments, PR intervals, QRS intervals, ST intervals, or QT intervals of the ECG data. In some embodiments, the first set of features comprises a standard deviation number of PR segments, ST segments, PR intervals, QRS intervals, ST intervals, or QT intervals of the ECG data.

In some embodiments, the state or condition of a heart is a valve disease. In some embodiments, the state or condition of a heart is an arrythmia. In some embodiments, the state or condition of a heart is a heart failure. In some embodiments, the state or condition of a heart is congenital heart disease.

Another aspect of the present disclosure presents a method for determining a state or condition of a heart of a subject, comprising: using a monitoring device comprising an electrocardiogram (ECG) sensor and an audio sensor to measure ECG data and audio data from the heart of the subject; transmitting the ECG data and the audio data wirelessly to a computing device; using a trained algorithm to process the ECG data and the audio data to determine the state or condition of the heart of the subject; providing an output indicative of the state or condition of the subject on the monitoring device.

In certain embodiments, the method further comprises providing a treatment plan based on the state or condition of the subject. In certain embodiments, the method further comprises providing an intervention plan based on the state or condition of the subject.

In some embodiments, the state or condition of a heart is a valve disease. In some embodiments, the state or condition of a heart is an arrythmia. In some embodiments, the state or condition of a heart is a heart failure. In some embodiments, the state or condition of a heart is congenital heart disease.

Another aspect of the present disclosure presents a method for determining a state or condition of an organ of a subject, comprising: using a monitoring device comprising an electrocardiogram (ECG) sensor and an audio sensor to measure ECG data and audio data from the heart of the subject; transmitting the ECG data and the audio data wirelessly to a computing device; using a trained algorithm to process the ECG data and the audio data to determine the state or condition of the heart of the subject; and providing an output indicative of the state or condition of the heart of the subject on the computing device.

In certain embodiments, the monitoring device is a mobile device. In certain embodiments, the computing device is a mobile device. In certain embodiments, the computing device is part of a cloud system. In certain embodiments, in (b) step of the method, the ECG data and the audio data are transmitted in a common packet.

In certain embodiments, providing the output indicative of the state or condition of the heart of the subject comprises a determining a presence or absence of a low ejection fraction of a left ventricle of the heart of the subject.

In certain embodiments, the ECG data comprises single-lead ECG data. In certain embodiments, the ECG data comprises three-lead ECG data. In certain embodiments, the ECG data comprises twelve-lead ECG data. In certain embodiments, the ECG data comprises chest cavity, lung, or intra-thoracic impedance measurement data.

In certain embodiments, in (c) of the method, the ECG data and the audio data are processed by one or more computer processors of the computing device. In certain embodiments, the method further comprises processing the ECG data and the audio data in a distributed computing system. In certain embodiments, in (c) step of the method, the ECG data and the audio data are processed in a distributed computing system.

In certain embodiments, the trained algorithm is a neural network. In certain embodiments, the state or condition of the heart of the subject is determined at an accuracy of at least about 90% for independent subjects. In certain embodiments, the accuracy is at least about 95%. In certain embodiments, the state or condition of the heart of the subject is determined to be a no-failure state or condition at a specificity of at least about 90% for independent subjects. In certain embodiments, the specificity is at least about 95%.

In certain embodiments, the state or condition of the heart of the subject is correlated with a magnitude and a duration of the audio data within a frequency band of the audio data. In certain embodiments, the output is an alert indicative of an adverse state or condition of the heart. In certain embodiments, the (a)-(d) are performed in a time period that is less than or equal to 1 minute.

In certain embodiments, the computing device is within about 30 feet of the monitoring device. In certain embodiments, the computing device is within about 10 feet of the monitoring device. In certain embodiments, the computing device is within about 5 feet of the monitoring device.

In certain embodiments, the state or condition of an organ or body part is a valve disease. In certain embodiments, the state or condition of an organ or body part is an arrythmia. In certain embodiments, the state or condition of an organ or body part is a heart failure. In certain embodiments, the state or condition of an organ or body part is congenital heart disease. In certain embodiments, the state or condition of an organ or body part is chronic obstructive pulmonary disease (COPD). In certain embodiments, the state or condition of an organ or body part is asthma. In certain embodiments, the state or condition of an organ or body part is pneumonia. In certain embodiments, the state or condition of an organ or body part is fistula. In certain embodiments, the state or condition of an organ or body part is inflammatory bowel disease (IBD).

Another aspect of the present disclosure provides a system for determining a state or condition of a heart of a subject. The system may comprise a communications interface configured to wirelessly communicate with a monitoring device, which monitoring device comprises an electrocardiogram (ECG) sensor and an audio sensor for measuring ECG data and audio data from the heart of the subject over a time period; and one or more computer processors operatively coupled to the communications interface, wherein the one or more computer processors are individually or collectively programmed to (i) receive the ECG data and the audio data wirelessly received by the communications interface from the monitoring device, and (ii) present the ECG data and the audio data on a user interface over the time period in substantially real time.

Another aspect of the present disclosure provides a system for determining a state or condition of a heart of a subject. The system may comprise a communications interface configured to wirelessly communicate with a monitoring device, which monitoring device comprises an electrocardiogram (ECG) sensor and an audio sensor for measuring (i) a first set of ECG data and audio data from the heart of the subject over a first time period, and (ii) a second set of ECG data and audio data from the heart of the subject over a second time period, wherein the second time period is different from the first time period; and one or more computer processors operatively coupled to the communications interface, wherein the one or more computer processors are individually or collectively programmed to (i) receive the first set of ECG data and audio data and the second set of ECG data and audio data, and (ii) process at least the first set of ECG data and audio data and the second set of ECG data and audio data to provide an output indicative of the state or condition of the heart of the subject on a user interface over at least the first time period and the second time period.

Another aspect of the present disclosure provides a system for determining a state or condition of a heart of a subject. The system may comprise a communications interface configured to wirelessly communicate with a monitoring device, which monitoring device comprises an electrocardiogram (ECG) sensor and an audio sensor for measuring ECG data and audio data, respectively, from the subject; and one or more computer processors operatively coupled to the communications interface, wherein the one or more computer processors are individually or collectively programmed to (i) receive the ECG data and the audio data wirelessly received by the communications interface from the monitoring device, (ii) use a trained algorithm to process the ECG data and the audio data to determine the state or condition of the subject, and (iii) provide an output indicative of the state or condition of the subject for display on a user interface.

Another aspect of the present disclosure provides a system for determining a state or condition of a subject. The system may comprise a communications interface configured to wirelessly communicate with a monitoring device, which monitoring device comprises an electrocardiogram (ECG) sensor and an audio sensor for measuring ECG data and audio data, respectively, from the subject; and one or more computer processors operatively coupled to the communications interface, wherein the one or more computer processors are individually or collectively programmed to (i) use the monitoring device to measure ECG data and audio data from the heart of the subject, (ii) wirelessly transmit the ECG data and the audio data to a computing device, (iii) remove noise from the audio data to yield processed audio data, (iv) process the ECG data and the processed audio data to determine the state or condition of the subject, and (v) output the state or condition of the subject.

Another aspect of the present disclosure provides a system for determining a state or condition of a heart of a subject, comprising: a communications interface configured to wirelessly communicate with a monitoring device, which monitoring device comprises an electrocardiogram (ECG) sensor and an audio sensor for measuring ECG data and audio data, respectively, from the subject; and one or more computer processors operatively coupled to the communications interface, wherein the one or more computer processors are individually or collectively programmed to (i) use the monitoring device to generate a first set of ECG data and/or audio data comprising a first plurality of features from the heart of the subject; (ii) transmit the first set of ECG data and/or audio data wirelessly to a computing device; (iii) use a trained algorithm to identify a plurality of sets of ECG data and/or audio data, wherein each of the plurality of ECG data and/or audio data comprises similar features to the first plurality of features; and (iv) provide an output containing a comparison between the first set of ECG data and/or audio data and the plurality of sets of ECG data and/or audio data.

Another aspect of the present disclosure provides a system for determining a state or condition of a subject, comprising: a communications interface configured to wirelessly communicate with a monitoring device, which monitoring device comprises an electrocardiogram (ECG) sensor and an audio sensor for measuring ECG data and audio data, respectively, from the subject; and one or more computer processors operatively coupled to the communications interface, wherein the one or more computer processors are individually or collectively programmed to (i) use the monitoring device to measure ECG data and audio data from the heart of the subject; (ii) wirelessly transmit the ECG data and the audio data to a computing device; (iii) process the ECG data and the audio data to determine the state or condition of the subject, and (iv) provide an output indicative of the state or condition of the subject on the monitoring device.

Another aspect of the present disclosure provides a system for determining a state or condition of an organ of a subject, comprising: a communications interface configured to wirelessly communicate with a monitoring device, which monitoring device comprises an electrocardiogram (ECG) sensor and an audio sensor for measuring ECG data and audio data from the heart of the subject; and one or more computer processors operatively coupled to the communications interface, wherein the one or more computer processors are individually or collectively programmed to (i) receive the ECG data and the audio data wirelessly received by the communications interface from the monitoring device, (ii) use a trained algorithm to process the ECG data and the audio data to determine the state or condition of the heart of the subject, and (iii) provide an output indicative of the state or condition of the heart of the subject on the computing device.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIG. 9 shows a summary of algorithm performance versus gold standard ECG data and versus heart murmur intensity.

FIG. 10 shows a summary of algorithm performance by pathology.

DETAILED DESCRIPTION

Figure 1:
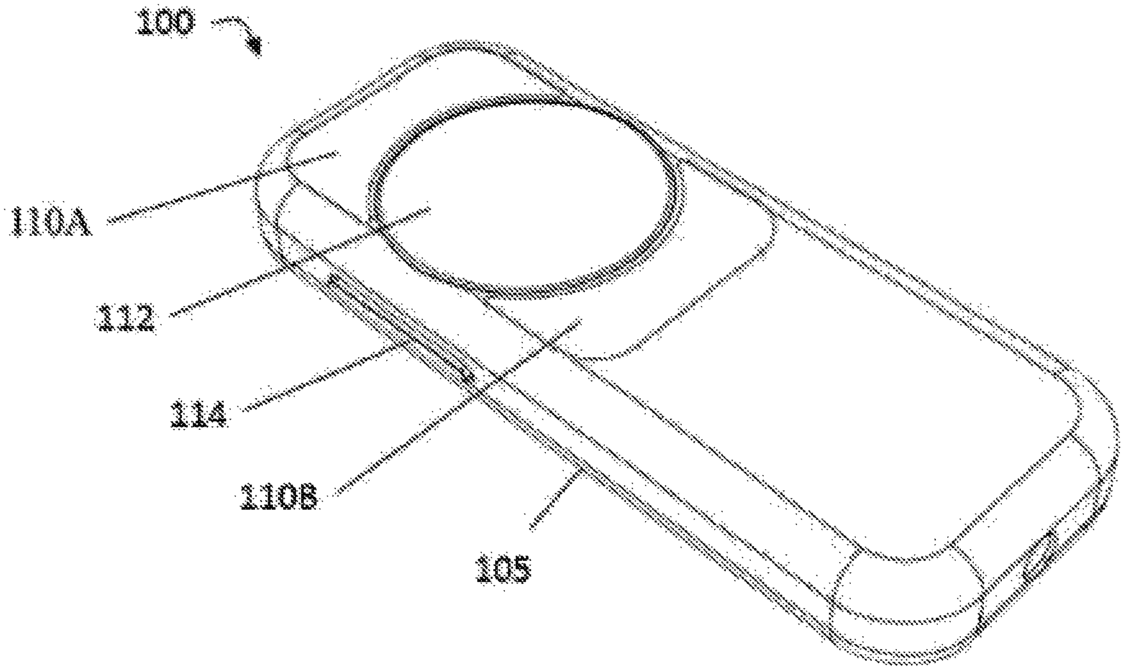
FIG. 1 shows a front perspective view of a monitoring device, in accordance with some embodiments.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Unless otherwise defined, all technical terms used herein have the same meaning as commonly understood to one of ordinary skill in the art to which this disclosure belongs. As used in this specification and the appended claims, the singular forms "a," "an," and "the" include plural references unless the context clearly dictates otherwise. Any references to "or" herein is intended to compass "and/or" unless otherwise stated.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The term "monitoring device," as used herein, generally refers to a device which comprises one or more sensors. A sensor may be selected from various sensing modalities. The sensor may be capable of measuring sensor data over time. The monitoring device may include multiple sensors of the same type, such as multiple electrocardiogram (ECG) sensors or audio sensors. As an alternative, the monitoring device may include multiple sensors of different types, such as an ECG sensor and an audio sensor. The monitoring device may be operable to connect to a remote device, such as a computing device. The computing device may be a mobile device. The computing device may be separate from or external to the monitoring device. The monitoring device may be operable to connect to a remote server. Analysis of data measured from the monitoring device may be done on the monitoring device or on a separate computing device (e.g., a mobile device and/or a server).

The term "state or condition," as used herein, generally refers to any classification which may be assigned to a subject or a part of a subject. The state or condition may comprise a disease state or healthy state. The state or condition may comprise a biological or physiological state or condition. The state or condition may comprise a particular diagnosis or determination. The state or condition may comprise an unknown state. Determining the state or condition of the subject may comprise determining the state or condition of an organ of the subject, such as, for example, a heart, lung, bowel, or other organ of the subject. For example, determining the state or condition of a heart may comprise a diagnosis or determination of a heart disease, disorder, or other condition such as low ejection fraction, congestive heart failure, heart murmur, valve disease, arrhythmia (e.g., bradycardia, tachycardia, ventricular tachycardia, ventricular fibrillation, premature ventricular contractions, supraventricular arrhythmia, superventricular tachycardia (SVT), paroxysmal superventricular tachycardia (PSVT), atrial fibrillation, Wolff-Parkinson-White Syndrome, atrial flutter, premature supraventricular contractions or premature atrial contractions (PACs), postural orthostatic tachycardia syndrome (POTS)), congenital heart disease, heart blockage, ischemia, infarction, pericarditis, hypertrophy, etc. The diagnosis or determination of a heart murmur can comprise a diagnosis or determination of a systolic murmur or a diastolic murmur. Further, systolic murmurs may comprise an aortic stenosis, a pulmonic stenosis, a mitral regurgitation, a tricuspid regurgitation, or a mitral valve prolapse, and more. Diastolic murmurs may comprise an aortic regurgitation, a pulmonic regurgitation, a mitral stenosis, or a tricuspid stenosis, and more. For example, determining the state or condition of a lung may comprise a diagnosis or determination of a lung disease, disorder, or other condition such as pneumonia, plural effusion, pulmonary embolism, poor airflow, chronic obstructive pulmonary disease (COPD), asthma, etc. For example, determining the state of condition of a bowel may comprise a diagnosis or determination of a bowel disease, disorder, or other condition such as inflammatory bowel disease (IBD), intestinal obstruction, hernia, infection within the digestive tract, etc.

The term "subject," as used herein, generally refers to an animal, such as a mammal (e.g., human) or avian (e.g., bird), or other organism, such as a plant. For example, the subject can be a vertebrate, a mammal, a rodent (e.g., a mouse), a primate, a simian, or a human. Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. The subject may be symptomatic with respect to a disease or condition. Alternatively, the subject may be asymptomatic with respect to the disease or condition. The subject can be a patient.

The term "algorithm," as used herein, generally refers to a process or rule for conducting a calculation or other problem-solving operation. An algorithm may be implemented by a computer, which may comprise one or more computer processors or circuitry for executing the algorithm, as described elsewhere herein. The algorithm may be a trained algorithm. The algorithm may be trained with one or more training sets, which may include data generated from subjects with known physiological or biological states or conditions. The trained algorithm may comprise a machine learning algorithm, such as a supervised machine learning algorithm or an unsupervised machine learning algorithm.

The term "real time," as used herein, can refer to a response time of less than or equal to about 1 second, a tenth of a second, a hundredth of a second, a millisecond, or less. The response time may be greater than about 1 second. In some instances, real time can refer to simultaneous or substantially simultaneous processing, detection, or identification.

Described herein are methods and systems for determining a physiological or biological state or condition of a subject, such as an organ of a subject. Such organ may be a heart, a lung, a bowel, or another organ or organ system (e.g., cardiovascular, pulmonary, gastrointestinal, or circulatory) of the subject.

Methods for Determining Physiological or Biological States or Conditions of a Subject In an aspect, the present disclosure provides methods for determining a physiological or biological state or condition of a subject, such as a heart, a lung, or a bowel of a subject. A method for determining a physiological or biological state or condition of a heart of the subject may comprise using a monitoring device comprising an electrocardiogram (ECG) sensor and an phonocardiogram (PCG) sensor (audio sensor) to measure ECG data and phonocardiography data (PCG data or audio data) from an organ of the subject. The ECG data and PCG data (audio data) may be transmitted to a computing device. The computing device may be separate from the monitoring device.

The ECG data and the PCG data (audio data) may be processed using a trained algorithm. The trained algorithm may comprise a neural network. The trained algorithm may correlate diagnostic features to a specific state or condition of an organ of a user. The trained algorithm may correlate a diagnostic feature to a specific state or condition using a frequency resolved analysis. The data may be analyzed on a computing device such as a remote server, cloud storage, or other connected device. In some cases, the computing device can be remote. The computing device may comprise a database of ECG and audio data associated with various states or conditions of different subjects or different organs of the same or different subjects. The trained algorithm may compare recorded ECG and audio data to at least pre-existing ECG and audio data of diseased and healthy subjects from its database.

Methods of the present disclosure may be performed in real time or substantially in real time. ECG data and audio data may be real-time streamed to a remote computing device such as a mobile device or a cloud storage. The data may be real-time streamed to a web browser. The data may be accessible to a remote user such as a health care provider. The data may be viewed remotely and in real-time by a health care provider. For example, the monitoring device may be synced in real time with a computing device, such as a mobile device. The computing device may relay the algorithm output to the clinician over the earpieces using voice, so that the clinician can hear the algorithm result.

The output of the trained algorithm may comprise displaying a graph, spectrogram, or other representation of the recorded audio or ECG data from an organ of a subject, such as a heart of a subject. The output may further comprise a result of processing such audio or ECG data or a combination thereof. For example, the output can comprise a prototypical heart beat sound after removing noises caused by subject motion, device motion, or other reasons in an audio wave form of a heartbeat. In some examples, the output may include an integrated acoustic cardiograph (ACG) report comprising interpretation of ECG data and sound data.

The output of the trained algorithm may comprise a dysfunction score which may be tracked by a subject and/or a health care provider longitudinally over time. Dysfunction scores are often calculated to provide a quantitative metric, a description or prediction of a state or condition of organs, such as a heart, lung, or bowel of a subject or a combination thereof. Dysfunction scores may be calculated for a single or multiple organs of a subject.

The output of the trained algorithm may comprise an audio feedback that may be heard over the earpiece(s) of the monitoring device. The output may be displayed on the computing device or monitoring device. The output may be accessible to the subject and a remote healthcare provider in real time or substantially real time. The output of the trained algorithm may comprise recommendations to the user or the healthcare provider. Recommendations may comprise follow-up tests or treatment recommendations, such as use of a particular therapeutic.

The methods of the present disclosure may be performed over various time periods. For example, methods of the present disclosure may be performed over a time that is less than or equal to about 6 months, 3 months, 2 months, 1 months, 3 weeks, 2 weeks 1 week 6 days, 5 days, 4 days, 3 days, 1 day, 12 hours, 6 hours, 5 hours, 4 hours, 3 hours, 2 hours, 1 hour, 30 minutes, 10 minutes, 5 minutes, 1 minute, 30 seconds, 10 seconds, 5 seconds, or less. As an alternative or in addition to, the time period may be at least about 5 seconds, 10 seconds, 20 seconds, 30 seconds, 1 minute, 5 minutes, 10 minutes, or more. Alternatively, such time period may be at most about 6 months, 3 months, 2 months, 1 months, 3 weeks, 2 weeks 1 week 6 days, 5 days, 4 days, 3 days, 1 day, 12 hours, 6 hours, 5 hours, 4 hours, 3 hours, 2 hours, 1 hour, 30 minutes, 10 minutes, 5 minutes, 1 minute, 30 seconds, 20 seconds, 10 seconds, 5 seconds, or less. The time period may be from about 1 second to 5 minutes, or about 5 seconds to 2 minutes, or about 10 seconds to 1 minute.

Multiple sets of ECG data and audio data may be measured over time periods which are different and/or temporally separate. In an example, a first set of ECG data and audio data from the heart of the subject may be measured over a first time period. Next, the first set of ECG data and audio data may be transmitted to a computing device. Next, the monitoring device may be used to measure a second set of ECG data and audio data over a second time period. The second time period may be different from the first time period. Finally, the second set of ECG data and audio data may be transmitted to the computing device.

Monitoring Devices

The present disclosure provides monitoring devices that may be used to collect data indicative of a physiological or biological state or condition of a subject, such as, for example, a heart, lung, or bowel of the subject. Such monitoring devices may be configured for use with computing devices described elsewhere herein.

FIG. 1 shows a monitoring device 100 comprising a housing 105, which encases sensors and control circuitry. The monitoring device 100 comprises a first sensor 110A and 110B of a first sensor modality, and a second sensor 112 of a second sensory modality. In the illustrated example, the first sensor 110A and 110B may comprise contact pads of an ECG sensor, and the second sensor 112 may comprise a surface for obtaining audio data. The second sensor 112 may include one or more piezoelectric ("piezo") units for collecting audio data.

The monitoring device may additionally comprise user controls such as button 114. Button 114 may control the intensity of a monitored signal to be transmitted to a user. Button 114 may comprise a positive end and a negative end, such that when the positive end (e.g. the upper portion) of the button is depressed, a signal amplitude is increased, and when a negative end (e.g. the lower portion) of the button is depressed, a signal amplitude is decreased. A signal amplitude may comprise a volume of an amplified audio signal. The audio signal may be transmitted wirelessly to an earpiece of a user (such as a healthcare provider) or of a subject.

Figure 2:
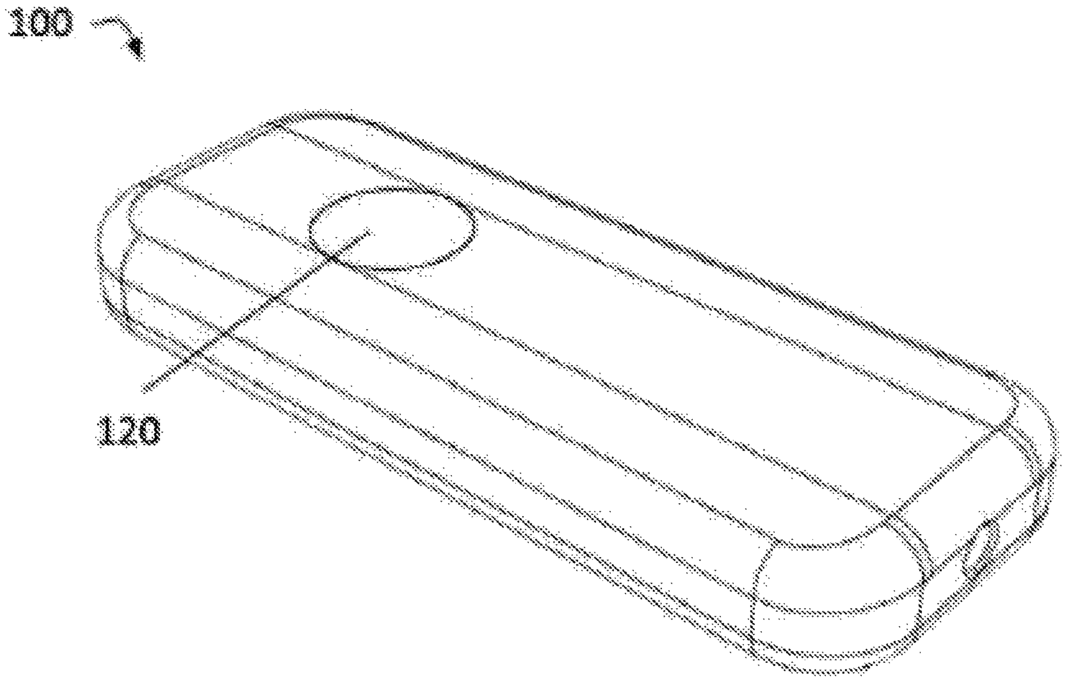
FIG. 2 shows a back perspective view of a monitoring device, in accordance with some embodiments.

FIG. 2 shows the back of the monitoring device of FIG. 1. The monitoring device 100 may comprise additional user controls such as button 120. Button 120 may be used to stop and start measurement of data by the monitoring device. Button 120 may be actuated by a user. It may be possible to stop or start measurement without actuation of button 120, such as by controlling collection through a computing device. The shape and design of sensor housing 105 may facilitate a subject's comfort during monitoring a state or condition of a subject. Additionally, the shape and design of sensor housing 105 may facilitate a secure fit against a variety of patient body types and shapes in order to improve sensor contact and with adequate sensor geometry.

The monitoring device may be mobile. For example, the monitoring device may be capable of movement from one point to another. The monitoring device may be capable of placement on and removal from a body of the subject. For example, the monitoring device may be placed adjacent to the body of the subject at a location in proximity to a heart, lung, or bowel of the subject. The monitoring device may not be implantable in the body of the subject. The monitoring device may be sufficiently light that it is easily transported from one location to another. For example, the device may weigh no more than about 0.5 pounds, 1 pound, 2 pounds, 3 pounds, 4 pound, 5 pounds, 6 pounds, 7 pounds, 8 pounds, 9 pounds, 10 pounds, or 50 pounds.

The monitoring device may be used to collect ECG data and/or audio data from a plurality of different locations or parts of a body of the subject, such as positions at and/or around a heart, lung, vein or artery of the subject. This may be performed by placing the monitoring device at different positions adjacent to the body of the subject (e.g., in contact with the body) and using the monitoring device to take one or more measurements (e.g., collect ECG data and/or audio data) at each of at least a subset of the different positions.

The monitoring device may be used to collect the audio data of the voice of the patient to evaluate the status of the lungs or heart.

The monitoring device may be used to input a sound into the patient and record the sound reflection to indicate the status of body tissue or fluid levels.

The monitoring device may be sufficiently sized such that it is easily transported from one location to another. The monitoring device may be handheld. The monitoring device may be of a size which may fit in a hand. For example, the monitoring device may comprise an external dimension of less than or equal to about 0.25 inches, 0.5 inches, 1 inch, 2 inches, 3 inches, 4 inches, 5 inches, 6 inches, 7 inches, 8 inches, 9 inches, 10 inches, 11 inches, 12 inches, or 24 inches.

Figure 3:
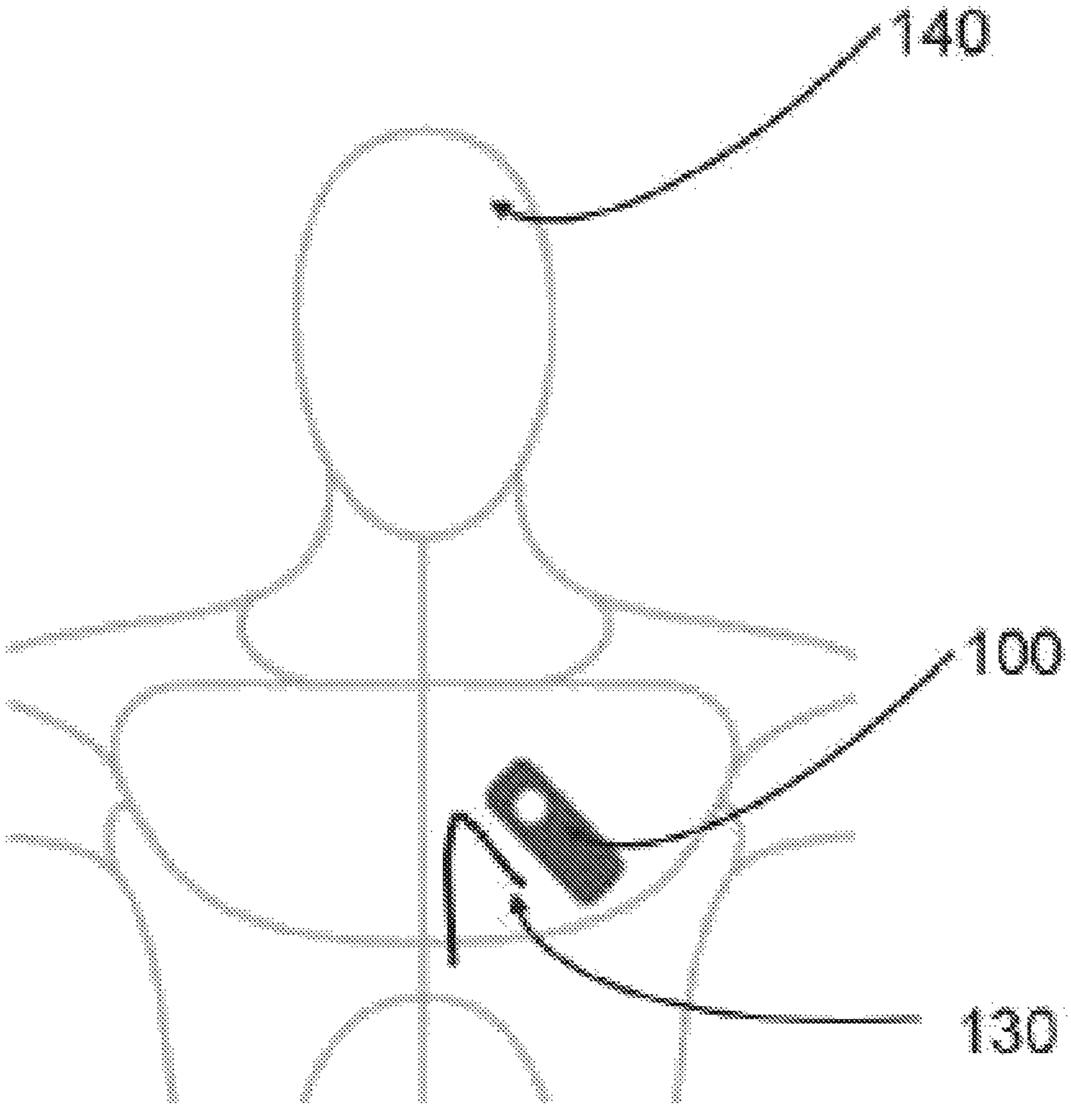
FIG. 3 shows schematic of a monitoring device placed external to a skin of a subject, in accordance with some embodiments.

FIG. 3 shows a monitoring device placed external to a skin of a subject. The monitoring device 100 may be positioned exterior to a skin of subject 140. The position of the monitoring device may be varied depending on the state or condition of a subject to be characterized. The subject to be characterized may be a human, such as a patient to be treated. The position of the monitoring device may be external to the skin near a subject's heart. The position of the monitoring device may be near a subject's lung. The position of the monitoring device may be near a subject's bowel. The position of the monitoring device may be near a subject's fistula (e.g., a diabetic fistula). The monitoring device may be placed near one or more areas of the head, chest, foot, hand, knee, ankle, or other body part exterior to the skin of a subject. The monitoring device may be used to obtain indications for venous access, which is one of the most basic but critical components of patient care both in hospital, in dialysis clinics, and in ambulatory patient settings. The monitoring device may be used to obtain indications of the flow rate or status of a fistula for venous access. The monitoring device may be used to obtain indications of lung fluid status for heart failure patients. The monitoring device may be used to obtain indications of cardiac filling pressure for heart failure patients. The device may be used to obtain indications to prescribe or not prescribe a medication based upon an output of the QT interval of the patient. The device may be used to obtain indications to change a medication dosage or frequency based upon the QT interval of the patient. The device may be used to obtain indications to change a heart failure medication prescription, dosage, or frequency, such as a diuretic or ace inhibitor, based upon the cardiac output, systolic time intervals, or lung fluid status.

It may be beneficial to place the monitoring device such that surface of both the first sensor and the second sensor is substantially in contact with the subject's skin. The sensors may be substantially in contact such that majority of the sensor surface is in contact with the subject skin. It may be beneficial to apply pressure onto the monitoring device directed toward the skin to order increase the surface area of the sensors in contact with the skin. Pressure may be applied by a subject or a third party. Sufficient pressure may be applied by a user with one hand; however, it may be possible to determine a state or condition of a patient without applying pressure to the monitoring device. It may be beneficial to apply a conductive gel to improve electrical contact between the sensor and the skin. A gel may be beneficial in cases where the subject has particularly dry skin or has significant body fat or hair.

The position of the monitoring device on a subject may be adjusted by rotating the device relative to the surface of the skin of the subject. The monitoring device may be placed at an angle 130. The angle 130 may be at least about 5, 10, 20, 30, 40, 45, 50, 60, 70, 80, 90, 100, 110, 120, 130, 140, 150, 160, 170, 180, 270, or greater degrees relative to the sternum, or any angle within by a range defined by any two of the preceding values.

Figure 13:
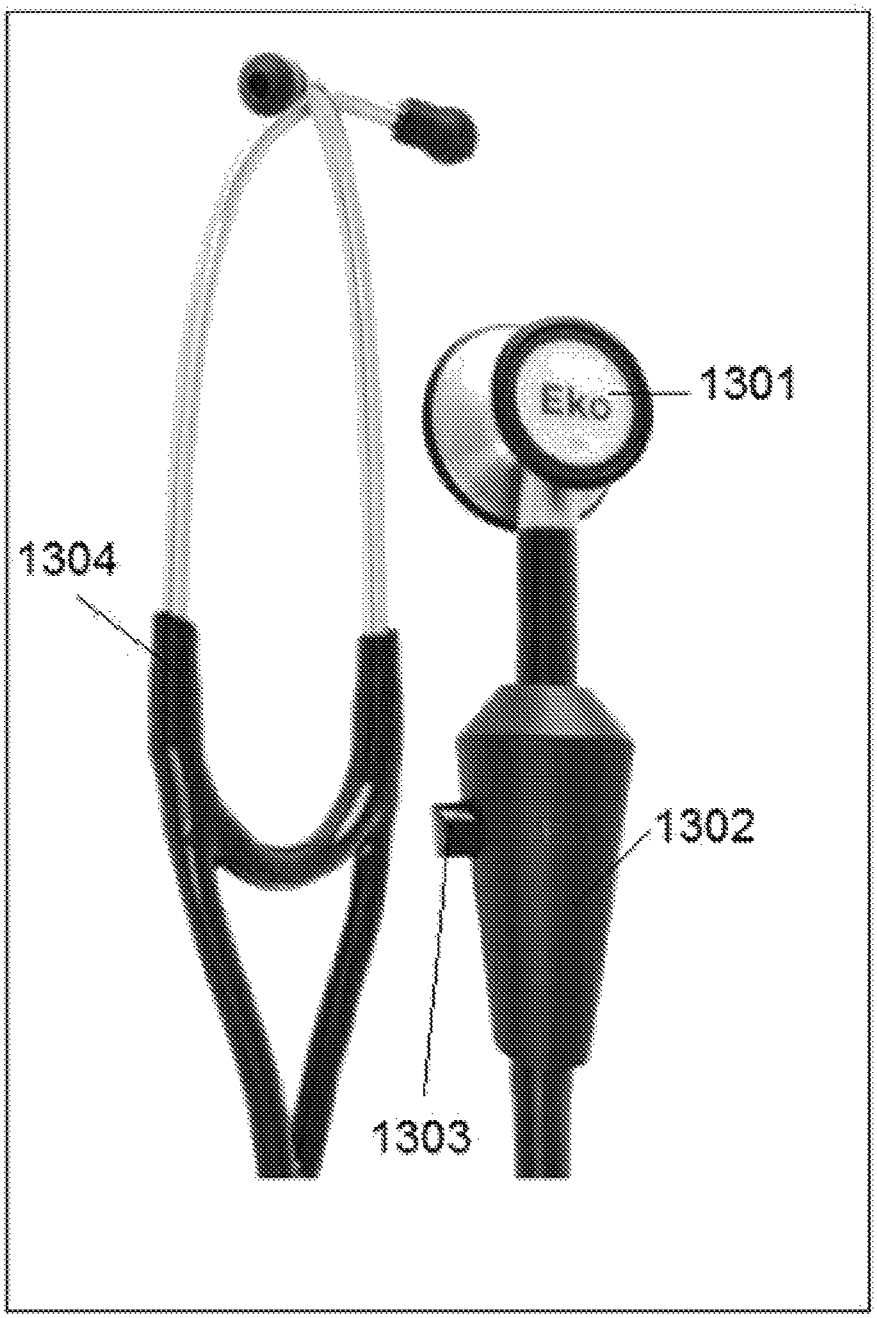
FIG. 13 shows a monitoring device comprising a stethoscope.

The monitoring device disclosed herein may also comprise a device 1300, as illustrated in FIG. 13. The device 1300 includes a resonator 1301 that is configured to be placed adjacent to a body of a subject. The resonator 1301 may be disc shaped. The resonator 1301 may be configured to collect audio information from a body of the subject. The resonator may include, for example, a piezoelectric unit and circuitry for collecting audio information from the body of the subject. The resonator 1301 may include circuitry with a communication interface that may be in communication (wired or wireless communication) with a transmitting unit 1302 that includes a button 1303. The device 1300 may comprise earpieces 1304. Earpieces may be used to listen to audio data as they are being generated. Earpieces may also be used to provide audio feedback generated by the trained algorithm to the user or the healthcare provider. Upon a user pressing the button 1303, audio information may be collected from the body of the subject and stored in memory and/or transmitted to a mobile device (e.g., mobile computer) in communication with the transmitting unit 1302.

Sensor Modalities

The monitoring device 100 may comprise sensors of one or a plurality of sensor modalities. The modalities may be operable to measure data from a subject. Examples of sensor modalities include electrical sensors (e.g., conductivity sensor, charge sensor, resistivity sensor or impedance sensor), audio sensors, accelerometers, light sensors, etc. The ECG sensor and the audio sensor may record ECG and audio data. The monitoring device may comprise at least two sensor modalities. Additionally or alternatively, the monitoring device may comprise at least three, at least 4, at least 5, or more sensor modalities. The monitoring device may comprise a plurality of sensors of each sensor modality. For example, the monitoring device may comprise at least about 1, 2, 3, 4, 5, 10, 20, 30, 40, 50, 100, 200, 300, 400, 500, or more sensors of any individual sensor modality. The number of sensors of a single modality may be the same; alternatively, there may be more or fewer sensors of one modality than another.

The monitoring device may include a housing having at least one ECG sensor and at least one audio sensor. The at least one ECG sensor may be integrated with the at least one audio sensor. The monitoring device may include at least about 1, 2, 3, 4, 5 or more ECG sensors, and at least about 1, 2, 3, 4, 5 or more audio sensors.

The first sensor modality may be an electrical sensor. The electrical sensor 110 may comprise a first electrode 110A and a second electrode 110B. Electrodes 110A and 110B may be physically separated by a distance to facilitate measurement of electrical signal from a subject. The distance between the first and second electrodes may be at least about 1 millimeter (mm), 2 mm, 5 mm, 10 mm, 20 mm, 50 mm, 100 mm, 200 mm, 500 mm, or more, or any distance defined by a range between any two of the preceding values. Electrodes 110A and 110B may comprise ECG transducer electrodes, which may measure electrical signals from a subject resulting from depolarization of the heart muscle during a heartbeat.

In some cases, the ECG data and audio data may be measured from the organ (e.g. heart, lung, or bowel) of the subject over a time period. Such time period may be at least about 5 seconds, 10 seconds, 20 seconds, 30 seconds, 1 minute, 5 minutes, 10 minutes, 30 minutes, 1 hour, 2 hours, 3 hours, 4 hours, 5 hours, 6 hours, 12 hours, 1 day, or more. Alternatively, such time period may be at most about 6 months, 3 months, 2 months, 1 months, 3 weeks, 2 weeks 1 week 6 days, 5 days, 4 days, 3 days, 1 day, 12 hours, 6 hours, 5 hours, 4 hours, 3 hours, 2 hours, 1 hour, 30 minutes, 10 minutes, 5 minutes, 1 minute, 30 seconds, 20 seconds, 10 seconds, 5 seconds, or less. The time period may be from about 1 second to 5 minutes, about 5 seconds to 2 minutes, about 10 seconds to 1 minute, about 1 minute to 10 minutes, about 10 minutes to 1 hour, or about 1 minute to 1 hour.

In some cases, the ECG data and audio data is measured from the organ (e.g. heart, lung, or bowel) of the subject over multiple time periods. The one or more time periods may be discontinuous. The one or more time periods may be temporally separate from other time periods. For example, the ECG and audio data may be measured over a first time period; the ECG data and audio data may be not be measured for an intervening period; and the ECG data and audio data may be measured over a second time period. The intervening period may be at least about 1 minute, 5 minutes, 10 minutes, 1 hour, 5 hours, 10 hours, 1 day, 1 week, 1 month, 1 year, 5 years, 10 years, or more. The intervening period may be from about 1 minute to 10 minutes, from about 1 minute to 1 hour, from about 5 minutes to 5 hours, from about 1 hour to 1 day, from about 1 day to 1 week, from about 1 week to 1 month, or from about 1 week to 1 year.

In some cases, many time periods may be separated by many intervening periods. In such a case, a longitudinal dataset comprising subject data may be collected. A longitudinal data set may be used to track a state or condition of a subject (such as the state or condition of a heart of a subject) over an extended period of time. A monitoring device may track an output comprising a state or condition of a subject over time. Additionally, a monitoring device may track a diagnostic feature of a subject over time. In some cases, ECG data from a first period may be compared to ECG data from a second period. In some cases, audio data from a first period may be compared to audio data from a second period. In some cases, combined datasets or features based on combined datasets may be compared.

A device of the present disclosure may include at least 1, 2, 3, 4, 5, 6, 7, 8, 9, 10, or more ECG electrodes. As an alternative or in addition to, the device may include at least 1, 2, 3, 4, 5, 6, 7, 8, 9, 10, or more audio sensors.

Figure 4:
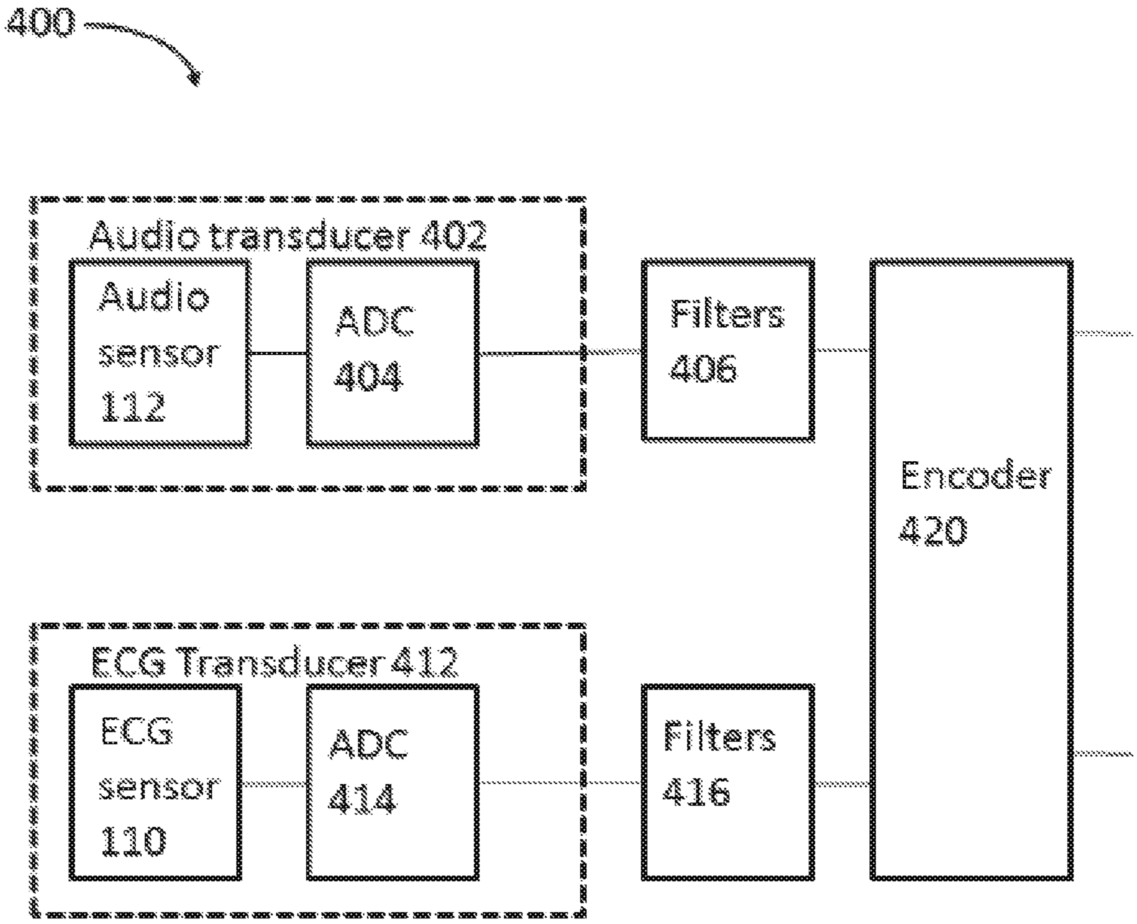
FIG. 4 shows a schematic of a sensor unit in the interior of a monitoring device.

FIG. 4 shows a schematic of a sensor unit 400 in the interior of a monitoring device. The first sensor may comprise an electrical sensor 110 configured to measure electrical data from a subject. The monitoring device may comprise an ECG transducer package 412. The package may comprise ECG electrodes 110A and 110B. The monitoring device may comprise an analog-to-digital converter (ADC) 414 to digitize ECG signals to detected by the ECG electrodes. The monitoring device may comprise signal processing circuitry to filter and condition detected signals. Signal processing circuitry may comprise filter 416. ECG data may be passed to an encoder 420. ECG signal processing circuitry may be implemented in the analog domain, in the digital domain, or both.

The ECG data may comprise single-lead ECG data. Single-lead ECG data may be obtained from one electrode that may be a ground and another electrode that may be a signal electrode. The voltage difference between the two leads may comprise analog ECG signal data. ECG data can be recorded as voltage as a function of time.

As an alternative, the ECG data may comprise three-lead ECG data. The three-lead ECG data may be obtained from three electrodes, which may comprise, for example, right arm, left arm, and left leg electrodes.

The ECG data may comprise five lead ECG data. The five-lead ECG data may be obtained from five electrodes, which may comprise, for example, right arm, left arm, left leg, right leg, and central chest electrodes. The ECG data may comprise twelve-lead ECG data. The twelve-lead ECG data may comprise twelve electrodes, which may comprise, for example, right arm, left arm, left leg, right leg, central chest (sternum), sternal edge right fourth intercostal space, sternal edge left fourth intercostal space, between V2 and V4, mid-clavicular line left fifth intercostal space, between V4 and V6 left fifth intercostal space, and mid-axillary line left fifth intercostal space electrodes. In some cases, the ECG data may comprise chest cavity, lung, and/or intra-thoracic impedance measurement data.

The electrical data may comprise ECG data measured from a heart of a subject. The electrical data may comprise impedance data measured from a lung or intra-thorax of a subject. The electrical data may comprise ECG data measured from a bowel or other organ of a subject. The electrical sensor may comprise a voltage sensitivity of greater than or equal to about 1 microvolt, 10 microvolts, 0.1 millivolts (mV), 0.2 mV, 0.5 mV, 1 mV, 2 mV, 5 mV, 10 mV, 50 mV, 100 mV or more.

The second sensor modality may be an audio sensor 112. The audio sensor may comprise a piezoelectric sensor. The audio sensor may comprise an electric-based sensor. The audio sensor may be configured to collect audio data. The audio data may comprise audio data of a heart of a subject. The audio data may comprise audio data of a lung of a subject. The audio data may comprise audio data of a bowel or other organ of a subject. The audio sensor may comprise a part of an audio transducer package. The monitoring device may comprise an analog-to-digital converter 404 to digitize audio signals detected by the audio sensor. The monitoring device may comprise signal processing circuitry to filter and condition detected signals. Signal processing circuitry may comprise filter 416. ECG data may be passed to an encoder 420. Audio signal processing circuitry may be implemented in the analog domain, in the digital domain, or both.

The audio sensor may comprise a frequency response of about 20 Hertz (Hz) to 20 kilohertz (kHz). The audio sensor may comprise a frequency response tuned to the low-frequency ranges between about 20 Hz and 2 kHz. The audio sensor may comprise a response to frequencies greater than or equal to about 5 Hz, 10 Hz, 20 Hz, 50 Hz, 100 Hz, 200 Hz, 500 Hz, 1 kHz, 2 kHz, 5 kHz, 10 kHz, 20 kHz, 50 kHz, 100 kHz, or more. The audio sensor may comprise a response to frequencies less than or equal to about 5 Hz, 10 Hz, 20 Hz, 50 Hz, 100 Hz, 200 Hz, 500 Hz, 1 kHz, 2 kHz, 5 kHz, 10 kHz, 20 kHz, 50 kHz, 100 kHz, or more. The audio sensor may comprise a response tuned to a range between about 20 Hz and 2 kHz, between about 15 Hz and 10 kHz, between about 10 Hz and 10 kHz, between about 10 Hz and 20 kHz, etc.

Figure 5:
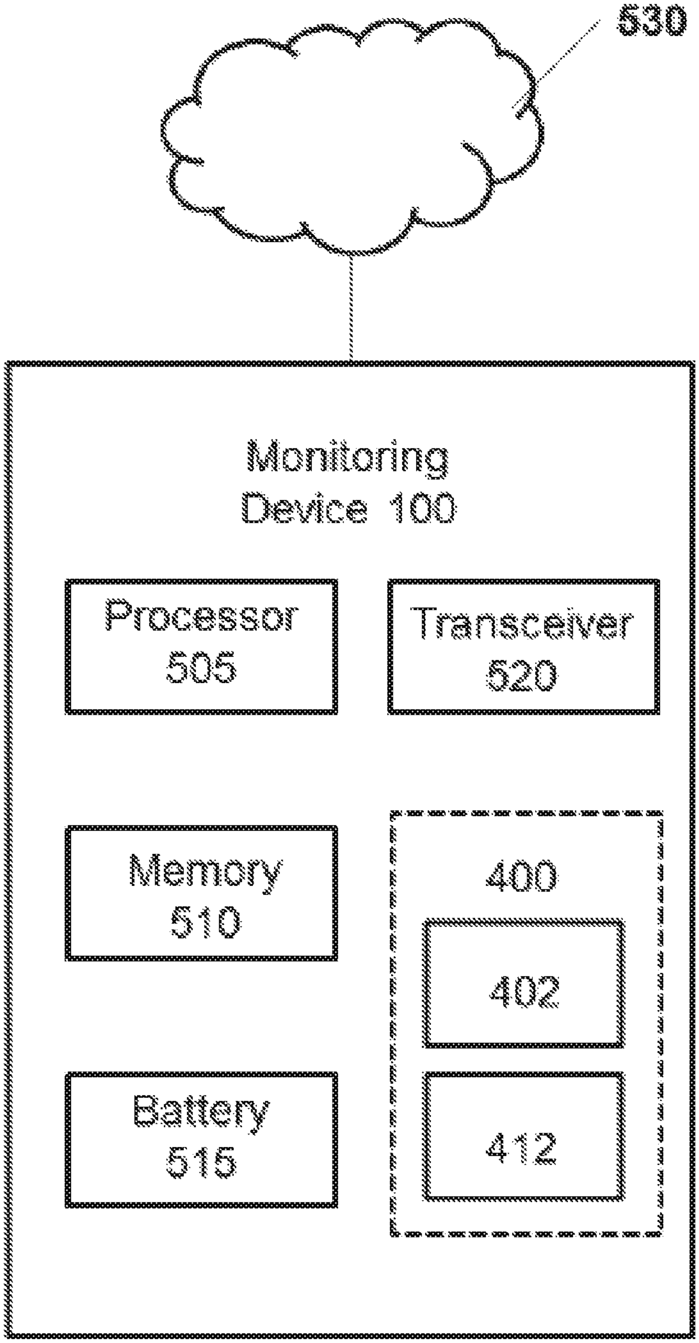
FIG. 5 shows a schematic of an interior of a monitoring device.

FIG. 5 shows a schematic of an interior of a monitoring device. The monitoring device may comprise electrical components necessary to control the operation of the various sensors. For example, the monitoring device may comprise devices to store data (e.g., hard drive or memory), to transmit data, to convert analog data to digital data, to provide information on the functionality of the monitoring device, to control various aspects of data collection, etc. The monitoring device may comprise a microprocessor or microprocessing unit (MPU) 505. The microprocessor may be operably connected to a memory 510. The MPU can execute a sequence of machine readable instructions, which can be embodied in a program or software. The instructions can be directed to the MPU, which can subsequently implement methods or components of methods of the present disclosure. Power may be supplied to the various components (the sensors, the microprocessors, the memory, etc.) by a battery 515. The battery may be coupled to wireless charging circuitry.

The monitoring device may transmit data to a computing device over a network 530. The monitoring device may comprise a transceiver 520 such as a wireless transceiver to transmit data to a computing device. The monitoring device may be connected to the Internet. The monitoring device may be connected to a cellular data network. A transceiver may comprise a Bluetooth transceiver, a WiFi radio, etc. Various wireless communication protocols may be utilized to convey data.

The monitoring device may store ECG data and audio data locally on the monitoring device. In an example, the ECG data and audio may be store locally on a memory 510 (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming.

The monitoring device may comprise electrical components necessary to process data from various sensors. For example, the monitoring device may comprise one or a plurality of the analog-to-digital converters (ADCs) 404 and 414. The one or a plurality of ADCs may sample the data from the various sensors such that electrical data is converted to a digital data stream. The monitoring device may comprise amplifier circuits and/or buffer circuits. The monitoring device may further comprise one or more components which compress the data of each sensor modality 420. The monitoring device may further comprise one or more components which filter data of each sensor modality 406 and 416.

In some cases, the ECG data and audio data comprise a temporal resolution. The temporal resolution may be dictated by the sample rate of the one or more ADCs. For example, the time between samples of the one or more ADCs may be less than or equal to about 0.01 microsecond, 0.02 microsecond, 0.05 microsecond, 0.1 microsecond, 0.2 microsecond, 0.5 microsecond, 1 microsecond, 2 microseconds, 5 microseconds, 10 microseconds, 20 microseconds, 50 microseconds, 100 microseconds, 200 microseconds, 500 microseconds, lmillisecond (ms), 2 ms, 5 ms, 10 ms, or more. Each of the ADCs may comprise its own sample rate which may be the same or different that other ADCs. Alternatively, one multi-channel ADC with a single sample rate may be used.

Data Structures

Figure 6:
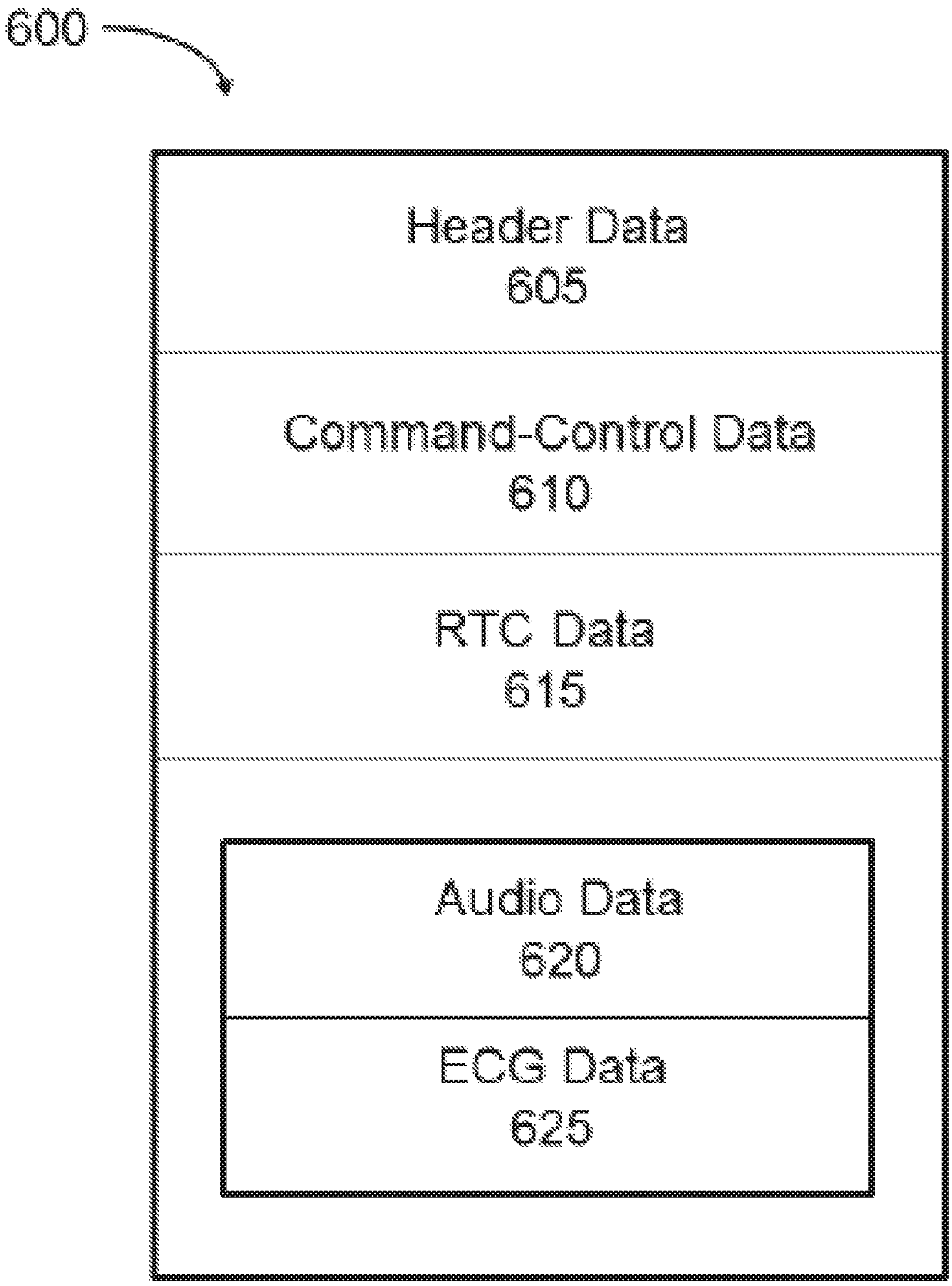
FIG. 6 shows an example packet structure for transmitting electrocardiogram (ECG) and audio data.

FIG. 6 shows an example of a packet structure for transmitting ECG and audio data. The monitoring device may transmit data via a wireless protocol, such as Bluetooth Low Energy protocol (BLE). The data may be transmitted in a packet structure 600. The transmitted data may comprise a reduced packet size in order to reduce power consumption. Packets may comprise multiple data dreams such as sound data, ECG data, and command and control data associated with the operation of the monitoring device and its interaction with the computing device.

The ECG data and the audio data may be transmitted from the monitoring device to the computing device in a common packet. The common packet may convey multiple types of medical instrument and control data via a low-bandwidth and low-power BLE communication link that can be received by standard smartphones, tablets, or other computing devices described elsewhere herein. The packet structure may convey sound data 620, ECG data 625, and command and control data 610 simultaneously, with sufficient fidelity for clinical use, within a single BLE packet.

Each packet may comprise a byte length provided for by the BLE standard and packet intervals compatible with commodity BLE chipsets and computing devices. A data structure may provide an effective bitrate of more than or equal to about 1 kilobit per second (kbps), 5 kbps, 10 kbps, 20 kbps, 100 kbps, 1 gigabit per second (Gbps), 5 Gbps, 10 Gbps, 20 Gbps, 100 Gbps, 1 terabit per second (Tbps), or more.

The packet may include header bytes 605, command and control bytes 610, and data bytes. The data bytes may comprise audio data bytes 620 and ECG data bytes 625. The audio data bytes may be used for transmitting sound data from an audio sensor such as the audio sensor described herein. The ECG data bytes may be used for transmitting electrical data from an electrical sensor such as the ECG sensor described herein.

In an example, the audio sensor converts an audio signal, such as heart, lung, or bowel sound data, into an analog electrical signal. An analog-to-digital converter (ADC) samples the output of the audio sensor and generates a digital data stream. The ADC may sample at a rate of at least about 4 kHz with at least 16-bit samples which may yield a least a 64-kbps audio stream. Audio compression may be applied by adaptive differential pulse-code modulation (ADPCM) to yield a 4-bit audio stream at a 4-kHz rate. With an 8-millisecond (ms) packet interval, each packet includes audio having 32 4-bit audio samples. However, the packet interval may comprise a period of at least about 1 microsecond, 2 microseconds, 5 microseconds, 10 microseconds, 20 microseconds, 50 microseconds, 100 microseconds, 200 microseconds, 500 microseconds, 1 ms, 2 ms, 5 ms, 10 ms, 20 ms, 50 ms, 100 ms, or more.

In another example, the ADC may sample at a rate of at least about 500 kHz, 1 kHz, 2 kHz, 3 kHz, 4 kHz, 5 kHz, 6 kHz, 7 kHz, 8 kHz, 9 kHz, 10 kHz, 100 kHz, or more. The ADC may take at least 2-bit, 4-bit, 8-bit, 16-bit, 32-bit, 64-bit, 128-bit, 256-bit samples, or more. Audio compression may compress the audio stream by a factor of at least about 2, 3, 4, 5, 6, 7, 8, 9, 10, 15, 20, 25, 30, 35, 40, 45, 50, 60, 70, 80, 90, 100, 150, 200, 1000, or more.

Digital filters can be applied to the output of ADC prior to ADPCM encoder in order to reduce artifacts and distortion during the ADPCM compression process. In an example, filters may include low-pass filters to attenuate high-frequency components above the set frequency. The frequency of the low-pass filter may comprise at least about 20 Hz, 50 Hz, 100 Hz, 500 Hz, 1 kHz, 2 kHz, 3 kHz, 4 kHz, 5 kHz, 6 kHz, 7 kHz, 8 kHz, 9 kHz, 10 kHz, 15 kHz, 20 kHz, or more. In an example, filters may include high-pass filters to attenuate low-frequency components below the set frequency. The frequency of the high-pass filter may comprise at least about 20 Hz, 50 Hz, 100 Hz, 500 Hz, 1 kHz, 2 kHz, 3 kHz, 4 kHz, 5 kHz, 6 kHz, 7 kHz, 8 kHz, 9 kHz, 10 kHz, 15 kHz, 20 kHz, or more. In other examples, the filters may comprise band pass filters, Fourier filters, or other filters. Frequency range limitations may be beneficial for purposes of medical diagnostics to reduced compression noise and artifacts from the ADPCM encoder.

ECG signals may be sampled by an analog-to-digital converter (ADC). The ECG signals may be sampled by the same ADC as the audio signals or a separate ADC. The audio ADC and the ECG ADC may comprise substantially similar characteristics. Alternatively, the sampling characteristics of the ECG ADC may be adapted for electrical data. In an example, the ADC may sample at a rate of at least about 500 Hz, 1 kHz, 2 kHz, 3 kHz, 4 kHz, 5 kHz, 6 kHz, 7 kHz, 8 kHz, 9 kHz, 10 kHz, 100 kHz, or more. The ADC may take at least about 2-bit, 4-bit, 8-bit, 16-bit, 32-bit, 64-bt, 128-bit, 256-bit samples or more. However, the packet interval may comprise a period of at least about 1 microsecond, 2 microseconds, 5 microseconds, 10 microseconds, 20 microseconds, 50 microseconds, 100 microseconds, 200 microseconds, 500 microseconds, 1 millisecond (ms), 2 ms, 5 ms, 10 ms, 20 ms, 50 ms, 100 ms, 500 ms, 1 second, or more.

The ECG data may be compressed. For example, compression may be applied by adaptive differential pulse-code modulation (ADPCM) or another data compression method. Data compression may compress the ECG data stream by a factor of at least about 2, 3, 4, 5, 6, 7, 8, 9, 10, 15, 20, 25, 30, 35, 40, 45, 50, 60, 70, 80, 90, 100, 150, 200, 1000, or more. The ECG data may be filtered. In an example, filters may include low-pass filters to attenuate high-frequency components above the set frequency. The frequency of the low-pass filter may comprise at least about 20 Hz, 50 Hz, 100 Hz, 500 Hz, 1 kHz, 2 kHz, 3 kHz, 4 kHz, 5 kHz, 6 kHz, 7 kHz, 8 kHz, 9 kHz, 10 kHz, 15 kHz, 20 kHz, or more. In an example, filters may include high-pass filters to attenuate low-frequency components below the set frequency. The frequency of the high-pass filter may comprise at least about 20 Hz, 50 Hz, 100 Hz, 500 Hz, 1 kHz, 2 kHz, 3 kHz, 4 kHz, 5 kHz, 6 kHz, 7 kHz, 8 kHz, 9 kHz, 10 kHz, 15 kHz, 20 kHz, or more. In other examples, the filters may comprise band pass filters, Fourier filters, or other filters.

Command-control data (alternatively command and control data) may comprise command data and/or control data. Command-control data may be implemented in header bits.

In an example, a header bit may comprise different command-control data for different packets with the same or similar bit size. A header bit or bits may be utilized to indicate which of multiple types of command-control data are conveyed within associated packet bit positions. For example, a header bit may include volume level, battery level, link integrity data, a time stamp, sequence number, etc.

Depending on the application, at least some or all command-control data may be sent in the header of every packet. For example, volume information may be sent at a fraction of the sample rate of the sensor data. A piece of command-control data stored in one or more header bits may be sent at rate less than the sensor data of at least about a factor of 2, 3, 4, 5, 6, 7, 8, 9, 10, 15, 20, 25, 30, 35, 40, 45, 50, 60, 70, 80, 90, 100, 150, 200, 1000, or more.

In examples where a given piece of command-control data is sent at a lower rate than the sample data, single header bit may be used to carry more than one type of data. For example, a piece of header data of type A may be sent in every-other packet in header bit 1, and a second piece of header data of type B may be sent in header bit 1 in the rest of the packets. By this method, the number of header bits required may be significantly reduced. Multiple header bits can be utilized to enable greater numbers of command-control data content types to be conveyed within a given packet bit position.

A computing device may display a warning on a user interface of the computing device. The warning may be indicative of a compromise in a link between the monitoring device and the computing device. It may be beneficial in medical applications to verify a link integrity. It may be desirable for devices to rapidly and reliable alert the user when a data transmission quality problem arises. A user may then remedy equipment problems and ensure that anomalous results are attributed to instrumentation error rather than the patient being monitored.

A rolling packet sequence may be inserted into the common packet structure. A rolling packet structure may comprise a link verification mechanism. The rolling packet structure may be disposed in the header bit of the packet structure. Predetermined bits within the header may be allocated to a rolling packet sequence indicator. The processor of the monitoring device may construct consecutive packets to increment through a rolling multi-bit packet sequence value. The computing device can decode the packet sequence value to verify that consecutive packets are received with sequentially incrementing packet sequence values.

A computing device may receive a sequential data packet having a non-sequential rolling packet sequence. In this case, the monitoring device may determine that a link has been compromised. The monitoring device may alert a user, such as a subject or a medical professional using an indication on the monitoring device. An indication on the monitoring device may comprise a light, a sound, a vibration, or other approach to alert a subject or another user. Additionally or alternatively, the monitoring device may indicate a compromised link through a communication with a remote computing device. In some cases, the monitoring device may send an alert to a remote computing device to alert a remote user.

Data may be presented on a user interface of a computing device in substantially real time. The packet structure may comprise additional header bits 615 in order to periodically send control data to a computing device to assure quality of data stream and synchronization between data streams. The runtime header bits may comprise a sequence number and/or a timestamp. The runtime header bits may include a reset bit to initialize or re-initialize the data compression. The runtime header bit may include device status information including battery charge, filtering state, volume level, and/or temperature. In some cases, the runtime header bits may comprise a portion of the command control data. The runtime header bits may comprise run time protocol. The runtime header bits may vary from packet to packet. The runtime header bits may vary based on a time of measurement. For example, the runtime header bit may change to provide an update of the status of a measurement, the monitoring device, a battery level, etc. For example, the runtime header data may be sent at a lower rate than the sample data to reduce size of the data stream.

Trained Algorithms

Methods and systems of the present disclosure can be implemented by way of one or more algorithms. An algorithm can be implemented by way of software upon execution by a processing unit of the monitoring device, the computing device, or a connected server. The algorithm may analyze ECG and/or audio data in order to provide an output indicative of a state or condition of an organ, such as a heart, a lung, or a bowel of a subject. The algorithm can, for example, be used to process the ECG data and the audio data to determine the physiological or biological state or condition of the heart of the subject.

In an example, the data may be processed by one or more computer processors of the computing device, described elsewhere herein. The data may comprise ECG data and audio data. An algorithm can be implemented upon execution by the processor of the monitoring device. Additionally or alternatively, an algorithm can be implemented upon execution by the processor of a connected server.

The algorithm may be a trained algorithm. The algorithm may be trained by a supervised or a guided learning method. For example, the trained algorithm may comprise a support vector machine, a decision tree, a stochastic gradient descent method, a linear discriminate analysis method, etc. Alternatively, the algorithm may be trained by an unsupervised learning method. For example, the algorithm may comprise clustering method, a decomposition method, etc. In an example, the learning method may be semi-supervised. Examples of learning algorithms include support vector machines (SVM), linear regression, logistic regression, naive Bayes, linear discriminant analysis, decision trees, k-nearest neighbor algorithm, random forests, and neural networks (or multilayer perceptron).

The algorithm may be trained by a training set that is specific to a given application, such as, for example classifying a state or condition (e.g., a disease). The algorithm may be different for heart disease and lung disease, for example. The algorithm may be trained for application in a first use case (e.g., arrythmia) using a training set that is different than training the algorithm for application in a second use case (e.g., pneumonia). The algorithm may be trained using a training set of subjects with known states or conditions (e.g., disorders). In some examples, the training set (e.g., type of data and size of the training set) may be selected such that, in validation, the algorithm yields an output having a predetermined accuracy, sensitivity and/or specificity (e.g., an accuracy of at least 90% when tested on a validation or test sample independent of the training set).

The trained algorithm may be a neural network. The neural network may comprise an unsupervised learning model or a supervised learning model. The audio and/or ECG data may be input into the neural network. Additional information such as age, gender, recording position, weight, or organ type may be inputted into the neural network. The neural network may output the likelihood of a pathology or disease, a disease severity score, an indication of lung dysfunction, an indication of heart failure, an indication of atrial fibrillation, an indication of different types of heart murmur, such as mitral regurgitation, tricuspid regurgitation, or other diseases or healthy states. In some cases, the neural network may be used to analyze the audio data, the ECG data, or both the audio and the ECG data.

Figure 11A:
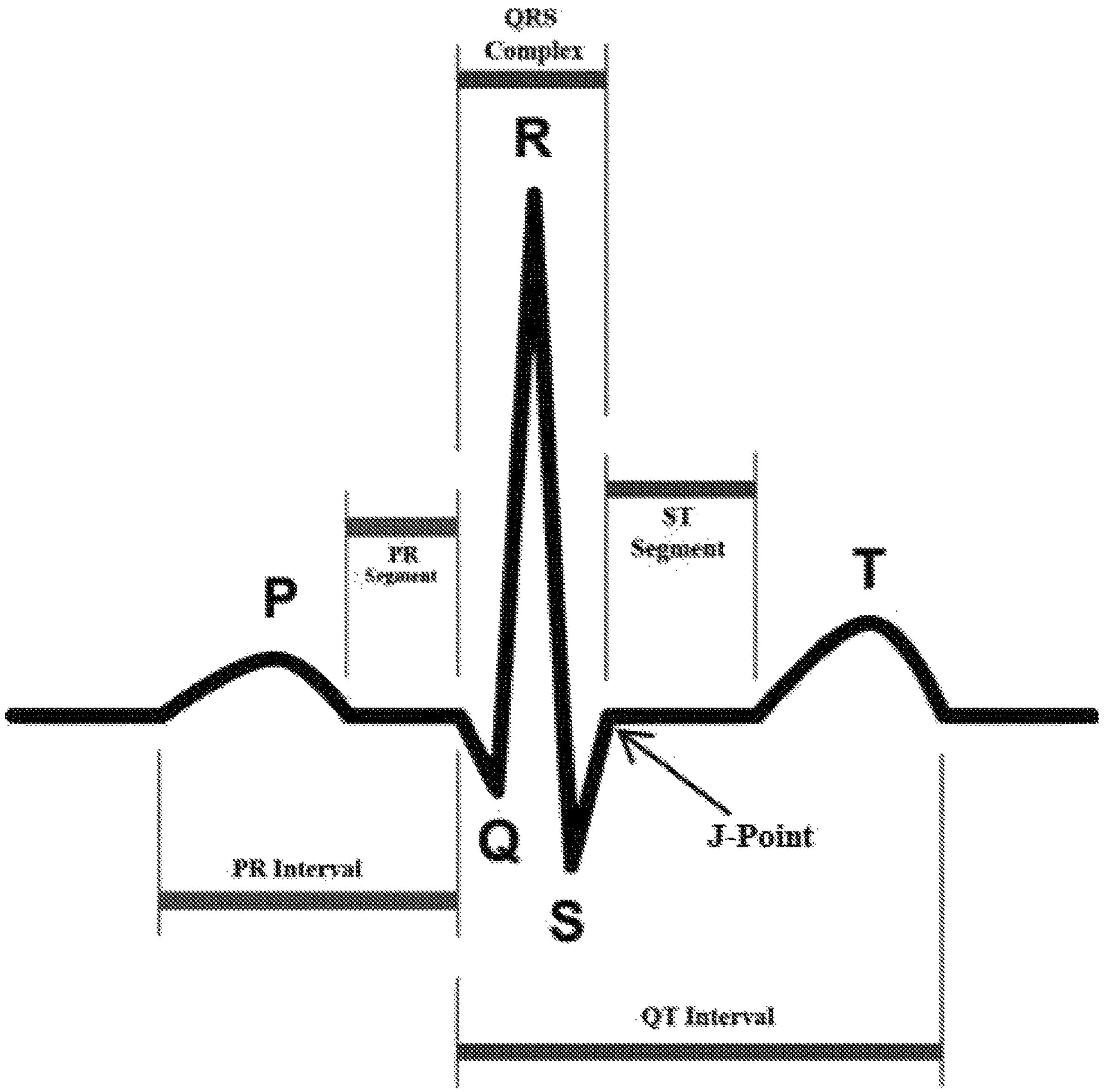
FIG. 11A shows a QRS complex from an example ECG diagram.
Figure 11B:
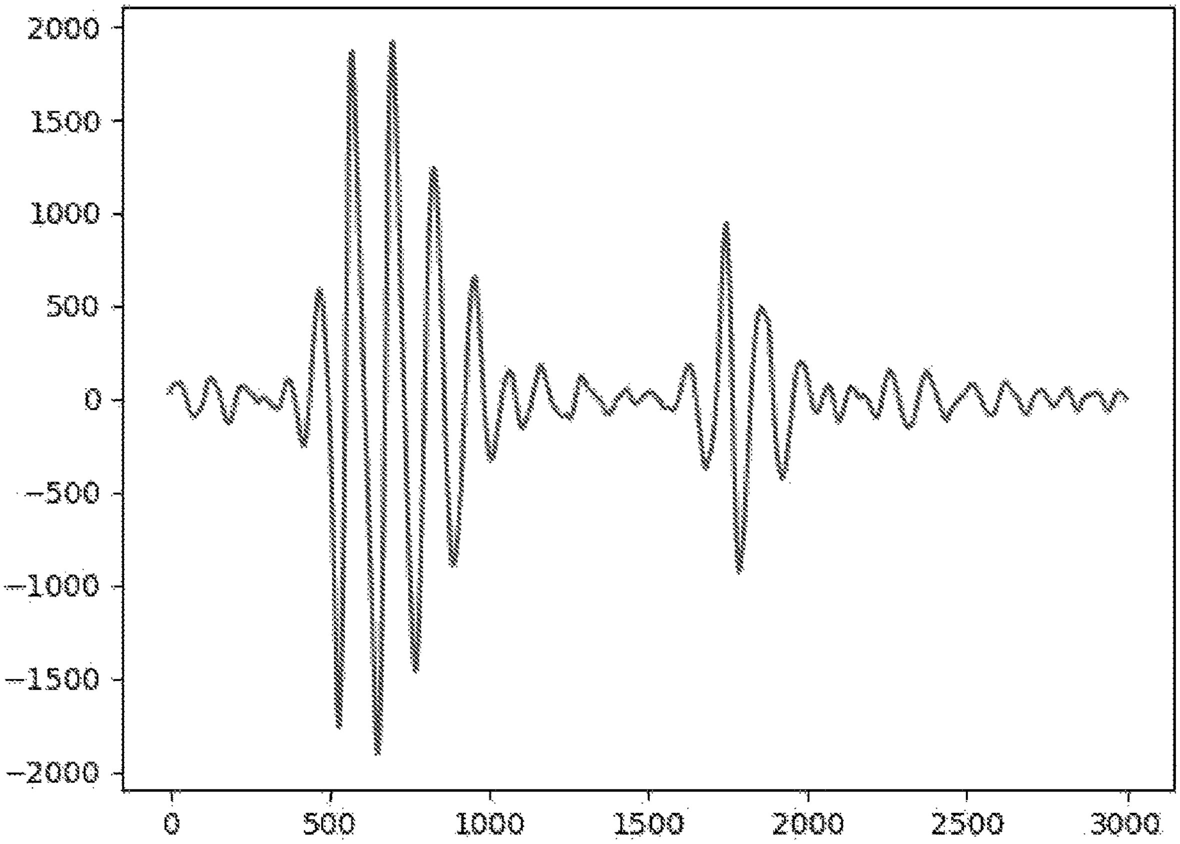
FIG. 11B shows an audio waveform of an example heartbeat with time 0 being an R-peak of a QRS complex from an ECG recorded from the same heartbeat.

The neural network may further use ECG data to cancel noise in audio data and create a clean representation of the audio data or otherwise process the audio data. The neural network may create different combinations of the audio and ECG data. For example, the audio signals recorded for a heartbeat of a subject can be noisy due to subject motion, device motion, or another reason. On a spectrogram of a waveform of the heartbeat can include peaks that are attributed to ambient noises even after sound filtering. The ECG data can be used to further remove noises after sound filtering in the audio data and provide a clean representation of the heart beat recorded. This may be performed by using the ECG data to trigger averaging of the audio data by comparing the QRS complex recorded by the ECG to the recorded audio signals. The QRS complex represents a combination of three of the graphical deflections seen on a typical ECG and can characterize a shape of a heartbeat signal. For example, an R-peak from the QRS complex (FIG. 11A) represents an ending of atrial contraction and a beginning of ventricular contraction. An audio waveform of a heartbeat typically represents a "lub-dub" sound. The "lub" sound occurs during the early phase of ventricular contraction and is produced by closing of the atrioventricular valves. Further, the "dub" sound occurs when the ventricles relax. Referring to FIG. 11B, time 0 of an audio waveform of a heartbeat can be matched to an R-peak in a QRS complex, thus peaks in the spectrogram of the waveform caused by noises can be disregarded.

Further, the neural network may be used to screen for a certain state or condition of a subject. The neural network may calculate a combined score to provide a quantitative metric for a state or condition of a subject comprising the combination of several metrics such as recorded ECG data, recorded audio data, data from other sensors such as a weight scale or an implantable sensor, user-input data, or data from other sources. Implantable sensors comprise implantable devices capable of providing real-time hemodynamic data such as Heart Failure (HF) systems further comprising CardioMEMS, right ventricular (RV) sensors, pulmonary artery (PA) sensors, and left atrial pressure (LAP) sensors, diagnostic features in implantable cardiac resynchronization therapy (CRT) devices and implantable cardioverter defibrillator (ICD) devices. Combined scores may directly or indirectly predict a state or condition of the subject such as detecting a low ejection fraction of the subject. Ejection fraction (EF) is a measurement, expressed as a percentage, of how much blood the left ventricle pumps out with each contraction. In a healthy state, an ejection fraction of a subject may be in the range between 55% and 70%. Low ejection fraction, or low EF, is the term used to describe an ejection fraction of a subject if it falls below 55%. Data and analysis from a neural network single lead ECG waveform, the presence and intensity of the third heart sound (S3) as detected by audio alone, ECG data alone, or a combination thereof, and the value of electromechanical activation time (EMAT) and can all be correlated to determine ejection fraction. The neural network may combine all of the three metrics to arrive at a combined score which is proportional to or related to the ejection fraction of the subject. In another example, the combined score can predict pulmonary artery pressure as measured by an implantable sensor like the CardioMEMS HF system.

In some cases, audio recordings may be manually labeled or annotated by physicians. The audio recordings may be manually labeled or annotated by data-scientists. In some cases, ECG data may be manually labeled or annotated by physicians. The ECG data may be manually labeled or annotated by data-scientists. The labeled data may be grouped into independent training, validation, and/or test data sets. The labeled data may be grouped such that all recordings from a given patient are included in the same set. The neural network may comprise a training dataset which has been classified. The neural network may be trained on a set of data comprising audio and ECG data with an assigned classification. A classification may comprise a dysfunction score. A classification may comprise a known diagnosis or determination. Alternatively, a classification may be assigned by a decomposition method such as singular value decomposition, principle component analysis, etc.

The trained algorithm may be configured to accept a plurality of input variables and to produce one or more output values based on the plurality of input variables. The plurality of input variables may comprise ECG data and/or audio data. The plurality of input variables may also include clinical health data of a subject. The one or more output values may comprise a state or condition of a subject (e.g., a state or condition of a heart, lung, bowel, or other organ or organ system of the subject). Further, in some examples, the trained algorithm may give more weight to certain characteristics of a state or condition. For example, for detecting heart murmur, the trained algorithm may be able to analyze identified sounds including S1, S2, and suspected murmurs. The trained algorithm may be able to analyze ECG data along with parameters such as, EMAT, left ventricular systolic twist (LVST), S3 strength, S4 strength, and SDI. For calculating hear rate and heart rate variability and the detection of atrial fibrillation, the trained algorithm may be able to analyze ambulatory ECG data and single-lead ECG signals.

The trained algorithm may comprise a classifier, such that each of the one or more output values comprises one of a fixed number of possible values (e.g., a linear classifier, a logistic regression classifier, etc.) indicating a classification of a state or condition of the subject by the classifier. The trained algorithm may comprise a binary classifier, such that each of the one or more output values comprises one of two values (e.g., {0, 1}, {positive, negative}, or {high-risk, low-risk}) indicating a classification of the state or condition of the subject. The trained algorithm may be another type of classifier, such that each of the one or more output values comprises one of more than two values (e.g., {0, 1, 2}, {positive, negative, or indeterminate}, or {high-risk, intermediate-risk, or low-risk}) indicating a classification of the state or condition of the subject.

The output values may comprise descriptive labels, numerical values, or a combination thereof. Some of the output values may comprise descriptive labels. Such descriptive labels may provide an identification or indication of a state or condition of the subject, and may comprise, for example, positive, negative, high-risk, intermediate-risk, low-risk, or indeterminate. Such descriptive labels may provide an identification of a treatment for the state or condition of the subject, and may comprise, for example, a therapeutic intervention, a duration of the therapeutic intervention, and/or a dosage of the therapeutic intervention suitable to treat the state or condition of the subject. Such descriptive labels may provide an identification of secondary clinical tests that may be appropriate to perform on the subject, and may comprise, for example, an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof. As another example, such descriptive labels may provide a prognosis of the state or condition of the subject. As another example, such descriptive labels may provide a relative assessment of the state or condition of the subject. Some descriptive labels may be mapped to numerical values, for example, by mapping "positive" to 1 and "negative" to 0.

Some of the output values may comprise numerical values, such as binary, integer, or continuous values. Such binary output values may comprise, for example, {0, 1}, {positive, negative}, or {high-risk, low-risk}. Such integer output values may comprise, for example, {0, 1, 2}. Such continuous output values may comprise, for example, a probability value of at least 0 and no more than 1. Such continuous output values may comprise, for example, an un-normalized probability value of at least 0. Such continuous output values may indicate a prognosis of the state or condition of the subject. Some numerical values may be mapped to descriptive labels, for example, by mapping 1 to "positive" and 0 to "negative."

Some of the output values may be assigned based on one or more cutoff values. For example, a binary classification of subjects may assign an output value of "positive" or 1 if the subject has at least a 50% probability of having the state or condition. For example, a binary classification of subjects may assign an output value of "negative" or 0 if the subject has less than a 50% probability of having the state or condition. In this case, a single cutoff value of 50% is used to classify subjects into one of the two possible binary output values. Examples of single cutoff values may include about 1%, about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, and about 99%.

As another example, a classification of subjects may assign an output value of "positive" or 1 if the subject has a probability of having the state or condition of at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more. The classification of subjects may assign an output value of "positive" or 1 if the subject has a probability of having the state or condition of more than about 50%, more than about 55%, more than about 60%, more than about 65%, more than about 70%, more than about 75%, more than about 80%, more than about 85%, more than about 90%, more than about 91%, more than about 92%, more than about 93%, more than about 94%, more than about 95%, more than about 96%, more than about 97%, more than about 98%, or more than about 99%.

The classification of subjects may assign an output value of "negative" or 0 if the subject has a probability of having the state or condition of less than about 50%, less than about 45%, less than about 40%, less than about 35%, less than about 30%, less than about 25%, less than about 20%, less than about 15%, less than about 10%, less than about 9%, less than about 8%, less than about 7%, less than about 6%, less than about 5%, less than about 4%, less than about 3%, less than about 2%, or less than about 1%. The classification of subjects may assign an output value of "negative" or 0 if the subject has a probability of the state or condition of no more than about 50%, no more than about 45%, no more than about 40%, no more than about 35%, no more than about 30%, no more than about 25%, no more than about 20%, no more than about 15%, no more than about 10%, no more than about 9%, no more than about 8%, no more than about 7%, no more than about 6%, no more than about 5%, no more than about 4%, no more than about 3%, no more than about 2%, or no more than about 1%.

The classification of subjects may assign an output value of "indeterminate" or 2 if the subject is not classified as "positive", "negative", 1, or 0. In this case, a set of two cutoff values is used to classify subjects into one of the three possible output values. Examples of sets of cutoff values may include {1%, 99%}, {2%, 98%}, {5%, 95%}, {10%, 90%}, {15%, 85%}, {20%, 80%}, {25%, 75%}, {30%, 70%}, {35%, 65%}, {40%, 60%}, and {45%, 55%}. Similarly, sets of n cutoff values may be used to classify subjects into one of n+1 possible output values, where n is any positive integer.

The trained algorithm may be trained with a plurality of independent training samples. Each of the independent training samples may comprise a dataset of ECG data and/or audio data collected from a subject at a given time point, and one or more known output values corresponding to the subject. Independent training samples may comprise datasets of ECG data and/or audio data and associated output values obtained or derived from a plurality of different subjects. Independent training samples may comprise datasets of ECG data and/or audio data and associated output values obtained at a plurality of different time points from the same subject (e.g., on a regular basis such as weekly, biweekly, or monthly). Independent training samples may be associated with presence of the state or condition (e.g., training samples comprising datasets of ECG data and/or audio data and associated output values obtained or derived from a plurality of subjects known to have the state or condition). Independent training samples may be associated with absence of the state or condition (e.g., training samples comprising datasets of ECG data and/or audio data and associated output values obtained or derived from a plurality of subjects who are known to not have a previous diagnosis of the state or condition or who have received a negative test result for the state or condition). A plurality of different trained algorithms may be trained, such that each of the plurality of trained algorithms is trained using a different set of independent training samples (e.g., sets of independent training samples corresponding to presence or absence of different states or conditions).

The trained algorithm may be trained with at least about 5, at least about 10, at least about 15, at least about 20, at least about 25, at least about 30, at least about 35, at least about 40, at least about 45, at least about 50, at least about 100, at least about 150, at least about 200, at least about 250, at least about 300, at least about 350, at least about 400, at least about 450, or at least about 500 independent training samples. The independent training samples may comprise datasets of ECG data and/or audio data associated with presence of the state or condition and/or datasets of ECG data and/or audio data associated with absence of the state or condition. The trained algorithm may be trained with no more than about 500, no more than about 450, no more than about 400, no more than about 350, no more than about 300, no more than about 250, no more than about 200, no more than about 150, no more than about 100, or no more than about 50 independent training samples associated with presence of the state or condition. In some embodiments, the dataset of ECG data and/or audio data is independent of samples used to train the trained algorithm.

The trained algorithm may be trained with a first number of independent training samples associated with presence of the state or condition and a second number of independent training samples associated with absence of the state or condition. The first number of independent training samples associated with presence of the state or condition may be no more than the second number of independent training samples associated with absence of the state or condition. The first number of independent training samples associated with presence of the state or condition may be equal to the second number of independent training samples associated with absence of the state or condition. The first number of independent training samples associated with presence of the state or condition may be greater than the second number of independent training samples associated with absence of the state or condition.

The data using may be modeled using a deep convolutional neural network architecture. The convolutional neural network may classify audio segments and/or ECG data segments over a measurement time. For example, the audio segments may be about 5 seconds long. For example, the audio segments may be within a range between about 0.1 second and 1 minute. The audio segments may be within a range between 1 second and 10 minutes. The audio seconds may be less than or equal to about 6 months, 3 months, 2 months, 1 months, 3 weeks, 2 weeks 1 week 6 days, 5 days, 4 days, 3 days, 1 day, 12 hours, 6 hours, 5 hours, 4 hours, 3 hours, 2 hours, 1 hour, 30 minutes, 10 minutes, 5 minutes, 1 minute, 30 seconds, 10 seconds, 5 seconds, 1 second, 100 milliseconds, or less. As an alternative or in addition, the audio segments may be at least about 100 milliseconds, 1 second, 5 seconds, 10 seconds, 20 seconds, 30 seconds, 1 minute, 5 minutes, 10 minutes, or more. Alternatively, such time period may be at most about 6 months, 3 months, 2 months, 1 months, 3 weeks, 2 weeks 1 week 6 days, 5 days, 4 days, 3 days, 1 day, 12 hours, 6 hours, 5 hours, 4 hours, 3 hours, 2 hours, 1 hour, 30 minutes, 10 minutes, 5 minutes, 1 minute, 30 seconds, 20 seconds, 10 seconds, 5 seconds, or less. The time period may be from about 1 second to 5 minutes, or from about 5 seconds to 2 minutes, or from about 10 seconds to 1 minute.

The model may comprise a number of layers. The number of layers may be between about 5 and 1000. The model may comprise at least about 1, 2, 3, 4, 5, 6, 7, 8, 9, 10, 11, 12, 13, 14, 15, 16, 17, 18, 19, 20, 21, 22, 23, 24, 25, 26 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 1000, 10000, 100000, 10000000, or more layers.

Each layer may comprise a one-dimensional convolution. Each layer may comprise a multidimensional convolution. Each layer may comprise a convolution with a dimensionality of at least about 1, 2, 3, 4, 5, 6, 7, 8, 9, 10, 11, 12, 13, 14, 15, 16, 17, 18, 19, 20, 21, 22, 23, 24, 25, 26 27, 28, 29, 30, 31, 32, 33, 34, 35, 36, 37, 38, 39, 40, 41, 42, 43, 44, 45, 46, 47, 48, 49, 50, or more. Each layer may comprise a stride and/or a padding. The stride and/or the padding may be adjusted such that the size of the output volume is manageable. In some cases, the padding may be zero. In some cases, the padding may be non-zero.

Each layer may comprise a rectified linear unit (ReLU) layer or an activation layer. However, in some cases, a hyperbolic tangent, sigmoid, or similar function may be used as an activation function. Each layer may be batch normalized. In some cases, the layers may not be batch normalized. In some cases, the network may comprise a pooling layer or a down sampling layer. In some cases, the pooling layer may comprise max pooling, average pooling, and L2-norm pooling, or similar. In some cases, the network may comprise a dropout layer. In some cases, the neural network comprises a residual neural network or ResNet. In some cases, the neural network may comprise skip-layer connections, or the neural network may comprise residual connections. Without being limited by theory, residual neural networks may help alleviate the vanishing gradient problem.

The neural network may be implemented using a deep learning framework in Python. In some cases, the neural network may use Pytorch & Torch, TensorFlow, Caffe, RIP, Chainer, CNTK, DSSTNE, DYNEt, Gensim, Gluon, Keras, Mxnet, Paddle, BigDL or similar deep learning framework. The neural network may be trained using TensorFlow, Google Cloud Machine Learning, Azure Machine Learning, Theano, GCT, Chainer, or similar.

The model may trained for a number of epochs which may be at least about 1, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 600, 700, 800, 900, 1000, 10000, 100000, or more. In some cases, regularization hyperparameters may be varied and evaluated based number of correct predictions on the validation set to determine a model with satisfactory performance. Model parameters may be iterated to achieve effective performance using an algorithm. The model parameters may use a stochastic gradient decent algorithm. The model parameters may be varied using an adaptive gradient algorithm, adaptive moment estimation, Adam, root mean square propagation, or similar. After each epoch, the classifier loss may be evaluated based on a validation set. The step size may be annealed by a factor of at least 2 after the validation loss has plateaued. In some cases, the step size may not be annealed. The model parameters from the epoch with the lowest overall validation loss may be selected for the model.

The model may be subsequently used to evaluate audio data alone, ECG data alone, or a combination of both to determine the presence or absence of a state or condition of an organ, such as a murmur of a heart. For example, the model may be used to detect a murmur of a heart based on the above criteria. The model may be further used to determine the type of the murmur detected. Heart murmurs may comprise systolic murmurs, diastolic murmurs, continuous murmurs, holosystolic or pansystolic murmurs, and plateau or flat murmurs. In some cases, the audio data may split into segments, as described herein with respect to training. The audio data over a period may be analyzed independently by the network. The network may output a probability of state or condition of a heart for each segment. These probabilities may then be averaged across all or a fraction of the segments. The average may then be thresholded to make a determination of whether a state or condition of an organ, such as a heart murmur is present.

Features of the audio data, the ECG data, or a combination of the audio and ECG data can be used to classify or determine a state or condition of the heart of a subject. Features of the recorded audio may comprise the intensity of audio frequency data, the pitch of the audio frequency data, change in the intensity of the audio frequency data over time also known as the shape of the audio frequency data, the location the signals are most intensely detected, the time during the audio cycle of the heart where the signals are detected, tonal qualities, and more. Further, features of the ECG diagram may comprise average numbers or standard deviation numbers of PR segments, ST segments, PR intervals, QRS intervals, ST intervals, or QT intervals.

For example, the state or condition of the heart of the subject may be correlated with a magnitude and a duration of the audio data within a frequency band of the audio data. A state or condition of a heart may be based on the magnitude and duration of audio in a specific frequency range. Particularly, the severity of a murmur of a heart may be correlated with the magnitude and duration of audio in a specific frequency band that is correlated with specific disease states. The magnitude or intensity of the audio may comprise a 6-point scale in evaluating heart murmurs. For example, absence of a heart murmur is graded as 0/6. Murmurs that are clearly softer than the heart sounds are graded 1/6. Murmurs that are approximately equal in intensity to the heart sounds are graded 2/6. Further, murmurs that are clearly louder than the heart sounds are graded 3/6. For score 4/6, the murmurs are easily audible and associated with a thrill. Moreover, a grade 6/6 is extremely loud and can be heard with a stethoscope even when slightly removed from the chest. Many other characteristics of sound can be used to evaluate heart murmurs as well. The pitch of the audio can be used to evaluate heart murmurs by classifying pitches as high, medium, or low. Tonal qualities such as blowing, harsh, rumbling, booming, sharp, dull or musical can also be used to evaluate heart murmurs.

The state or condition of the heart of the subject may be correlated with a certain audio frequency at a certain time during the audio cycle of the heart. The audio cycle of heart comprises normal heart sounds S1 and S2. The duration of time between S1 and S2 is called systole. The duration of time between S2 and the next S1 in the cycle is called diastole. Extra heart sounds S3 and S4 may be detected during the audio cycle of the heart which may be correlated with a state or condition of the heart, such as a diagnosis. Heart sounds or signals detected during the systole may be correlated with systolic conditions. Heart sounds or signals detected during the diastole may be correlated with diastolic conditions. Heart sounds may comprise continuous sounds during the audio cycle of the heart which may be correlated with certain states or conditions of the subject. The state or condition of the heart of the subject may be correlated with the change in the intensity of the audio signals over time. The intensity of audio signals over time can also be demonstrated by various shapes. Shapes of audio signals, which can also be used to classify murmurs, comprise crescendo, decrescendo, crescendo-decrescendo, or plateau, also known as flat. Crescendo signals increase over time. Decrescendo signals decrease over time. Crescendo-decrescendo means the intensity of the signals initially increases over time, but after a certain time starts to decrease over time. Plateau or flat signals remain stable over time.

Figure 12:
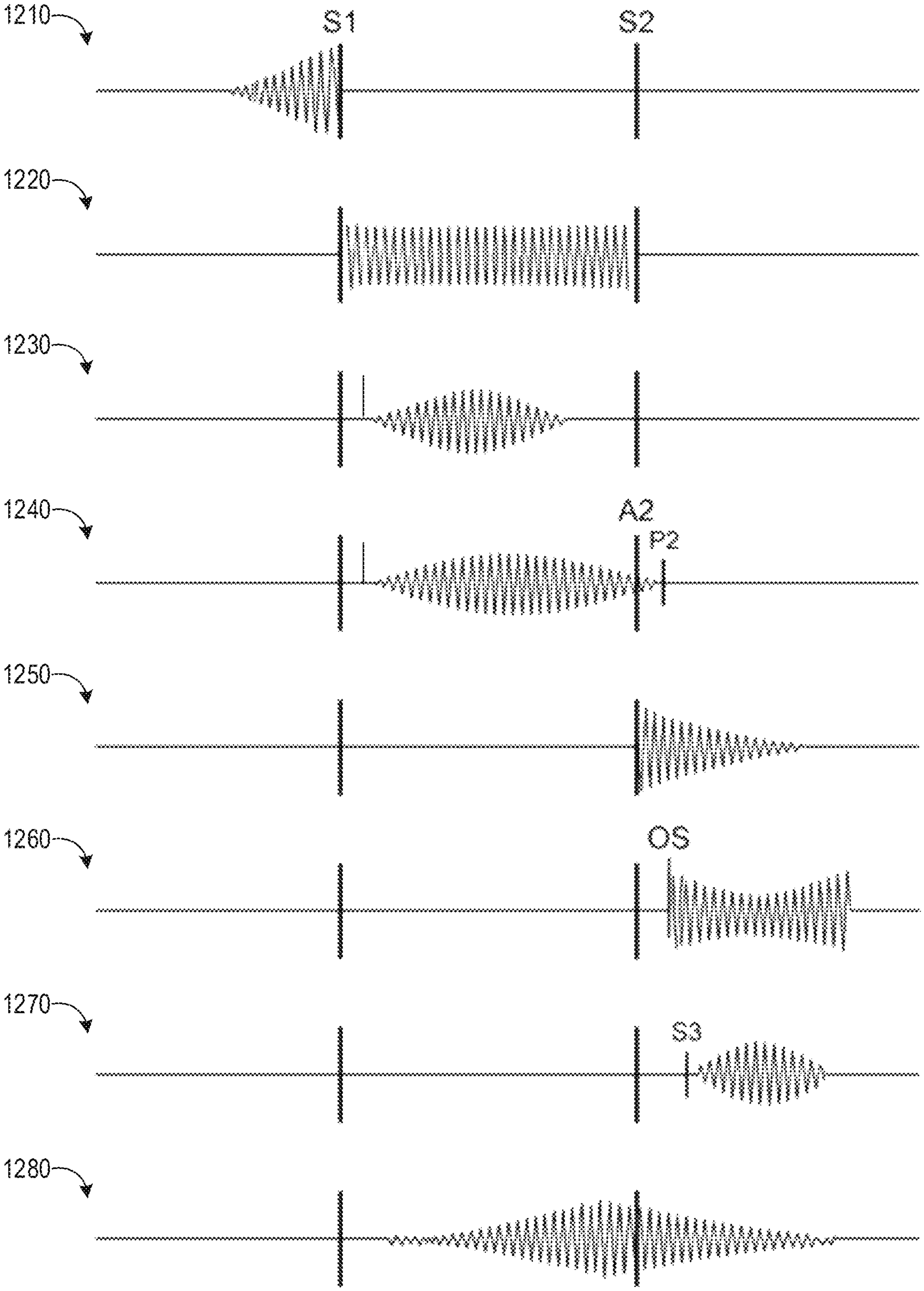
FIG. 12 shows examples of various heart murmurs with various shapes.

FIG. 12 shows examples of various heart murmurs. Panel 1210 depicts a presystolic crescendo murmur of mitral or tricuspid stenosis. Panel 1220 depicts a holosystolic(pansystolic) flat/plateau murmur of mitral or tricuspid regurgitation or of ventricular septal defect. Panel 1230 depicts a crescendo-decrescendo aortic ejection murmur beginning with an ejection click and fading before the second heart sound. Panel 1240 depicts a crescendo-decrescendo systolic murmur in pulmonic stenosis spilling through the aortic second sound, pulmonic valve closure being delayed. Panel 1250 depicts a decrescendo aortic or pulmonary diastolic murmur. Panel 1260 depicts a long diastolic murmur of mitral stenosis after an opening snap. Panel 1270 depicts a short mid-diastolic inflow murmur after a third heart sound. Panel 1280 depicts a continuous murmur of patent ductus arteriosus.

The state or condition of the heart may be correlated with the location in a subject where the signal is most loudly or intensely detected. For example, the audio may be most intensely detected in the aortic region, the pulmonic region, the mitral region also known as the apex, the tricuspid region, the left sternal border in the intercostal space of the subject or along the left side of the sternum or other locations in the subject. Therefore, these locations may be the best for detecting a heart murmur.

In addition, features of audio data, ECG data, or a combination of audio and ECG data can also be used to classify and evaluate other states or conditions of a subject. Examples of states or conditions of a subject comprise aortic stenosis, pulmonic stenosis, mitral regurgitation, tricuspid regurgitation, mitral valve prolapse, aortic regurgitation, pulmonic regurgitation, mitral stenosis, tricuspid stenosis, volume overload, pressure overload or atrial gallop. Aortic stenosis is a systolic heart murmur correlated with a crescendo-decrescendo audio frequency detected after the first normal heart sound S1 and before the second normal heart sound S2 in the audio cycle of the heart, most intensely detected in the aortic region in the intercostal space of the subject. Pulmonic stenosis is a systolic heart murmur correlated with a crescendo-decrescendo audio frequency detected after the first normal heart sound S1 and before the second normal heart sound S2 in the audio cycle of the heart most intensely detected in the aortic region in the intercostal space of the subject. Mitral regurgitation is a holosystolic heart murmur correlated with a plateau/flat audio frequency detected after the first normal sound S1, late in the systole, most intensely detected in the mitral region/apex of the intercostal space of the subject. Tricuspid regurgitation is a holosystolic murmur correlated with a plateau/flat audio frequency detected after the first normal sound S1 and before the second normal sound S2 in the audio cycle of the heart, most intensely detected in the tricuspid region of the intercostal space of the subject. Mitral valve prolapse is a systolic murmur associated with a mid-systolic non-ejection click most intensely detected in the mitral region/apex of the intercostal space of the subject. Aortic regurgitation is a diastolic heart murmur correlated with a decrescendo audio frequency detected after the second normal heart sound S2 most intensely detected in the left sternal border in the intercostal space of the subject. Pulmonic regurgitation is a diastolic heart murmur correlated with a decrescendo audio frequency after the second normal heart sound S2 most intensely detected along the left side of the sternum. Mitral stenosis is a diastolic heart murmur correlated with an audio frequency after the second normal heart sound most intensely detected in the mitral area or the apex, also correlated with an opening snap followed by a mid-diastolic rumble or rumbling sound in the diastole during the audio cycle of the heart. Tricuspid stenosis is a diastolic heart murmur correlated with an audio frequency after the second normal heart sound S2 most intensely detected in the tricuspid area in the intercostal space of the subject.

The frequency may correlate with turbulent blood flow caused by a narrowing of a valve in the heart. The frequency may correlate with blood flow caused by a hole between two chambers of the heart. The frequency may correlate with blood flow through a narrowed coronary artery. The frequency may correlate with regurgitation in the blood flow. The frequency may correlate with impaired cardiac muscle function. The frequency may correlate with the ECG data to indicate cardiac muscle function. The frequency data may comprise a correlation with heart failure including congestive heart failure diagnosis or other cardiovascular conditions.

The ECG and/or audio data may comprise features associated with known pathologies. Features associated with known pathologies may comprise diagnostic features. The ECG and/or audio data may be reduced in size by determining a set of diagnostic features from the data. The diagnostic features may comprise factors known to effect diagnostic outcomes such as an average or a standard deviation of time interval between heart beats, the average or standard deviation in an amplitude of an ECG signal associated with a heart contraction, etc. An average or standard deviation of one or more of a QT interval, ST segment, PR interval, PR segment, QRS complex, etc. Alternatively, a set of features may be determined by a spectral decomposition of an ECG and/or audio data set. In an example, a diagnostic feature is assigned by a user, such as a health care provider. The ECG data may be correlated with atrial fibrillation through the presence or absence of characteristic ECG waves. The ECG data may be correlated with heart failure through a relationship with the heart sounds. The ECG data may be correlated with systolic function in the heart through wave lengths or ECG interval durations. The ECG data may be correlated with fluid status in the lungs through intra-thoracic impedance measurements.

An output indicative of the physiological or biological state or condition of the heart of the subject may then be provided on the computing device. The output may be an alert indicative of an adverse state or condition of the heart. In an example, an output indicative of the state or condition of the heart of the subject may comprise a presence or absence of a low ejection fraction of a left ventricle of the heart of the subject. An output of the state or condition of a heart of a subject may comprise an indicator of systolic function.

Determining the state or condition of the subject may comprise determining the state or condition of an organ of the subject, such as a heart or a lung of the subject. The state or condition of various parts of a body of the subject may be determined. Determining the state or condition of a heart of a subject may comprise a diagnosis or determination of low ejection fraction, congestive heart failure, heart murmur, arrhythmia, heart blockage, ischemia, infarction, pericarditis, hypertrophy, or determining or predicting the pressure of the pulmonary artery, or other states or conditions of the subject. Determining the state or condition of a lung may comprise a diagnosis or determination of pneumonia, plural effusion, pulmonary embolism, poor airflow, chronic obstructive pulmonary disease, etc. The ECG and audio data may detect the presence of fluid, crackles or gurgles in the lung. The neural network may compare the lung sounds to diseased and healthy conditions of example lungs.

Determining the state of condition of a bowel comprises a diagnosis or determination of inflammatory bowel disease, intestinal obstruction, hernia, infection within the digestive tract, etc. The output may provide an indication of gastric motility or bowel function.

The state or condition of an organ of the subject may be determined at an accuracy of at least about 80%, 85%, 90%, 95%, 98%, 99%, or more for independent subjects. For example, the state or condition of the heart of the subject may be determined at an accuracy of at least about 80%, 85%, 90%, 95%, 98%, 99%, or more. For example, the state or condition of the lung of the subject may be determined at an accuracy of at least about 80%, 85%, 90%, 95%, 98%, 99%, or more. For example, the state or condition of the bowel of the subject may be determined at an accuracy of at least about 80%, 85%, 90%, 95%, 98%, 99%, or more. The state or condition of the subject may comprise an output of a trained algorithm, such as a neural network.

The state or condition of the organ of the subject may be determined at a specificity of at least about 80%, 85%, 90%, 95%, 98%, 99%, or more. The state or condition of the organ of the subject may be determined at a sensitivity of at least about 80%, 85%, 90%, 95%, 98%, 99%, or more. The state or condition of the organ of the subject may be determined at a specificity of at least about 80%, 85%, 90%, 95%, 98%, 99%, or more, and a sensitivity of at least about 80%, 85%, 90%, 95%, 98%, 99%, or more. The state or condition of the organ of the subject may be determined at a positive predictive value of at least about 80%, 85%, 90%, 95%, 98%, 99%, or more. The state or condition of the organ of the subject may be determined at a negative predictive value of at least about 80%, 85%, 90%, 95%, 98%, 99%, or more. The state or condition of the organ of the subject may be determined at an accuracy of at least about 80%, 85%, 90%, 95%, 98%, 99%, or more. The state or condition of the organ of the subject may be determined with an area under the receiver operating characteristic (AUROC) of at least about 0.75, 0.80, 0.85, 0.90, 0.95, 0.98, 0.99, or more.

The state or condition of an organ of the subject may be determined to be a no-failure state or condition at a specificity of at least about 80%, 85%, 90%, 95%, 98%, 99%, or more for independent subjects. For example, the state or condition of a heat of the subject may be determined to be a no-failure state or condition at a specificity of at least about 80%, 85%, 90%, 95%, 98%, 99%, or more for independent subjects. For example, the state or condition of a lung of the subject may be determined to be a no-failure state or condition at a specificity of at least about 80%, 85%, 90%, 95%, 98%, 99%, or more for independent subjects. The state or condition of a bowel of the subject may be determined to be a no-failure state or condition at a specificity of at least about 80%, 85%, 90%, 95%, 98%, 99%, or more for independent subjects. The state or condition of the heart in relation to heart murmurs such as mitral regurgitation (MR), or tricuspid regurgitation may be detected with greater than about 95% sensitivity and specificity. The state or condition of the heart in relation to atrial fibrillation may be detected with greater than 99% sensitivity and specificity. The state or condition of the heart in relation to congestive heart failure or heart failure may be detected with greater than 95% sensitivity and specificity.

The trained algorithm may be configured to identify the state or condition at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more; for at least about 5, at least about 10, at least about 15, at least about 20, at least about 25, at least about 30, at least about 35, at least about 40, at least about 45, at least about 50, at least about 100, at least about 150, at least about 200, at least about 250, at least about 300, at least about 350, at least about 400, at least about 450, or at least about 500 independent training samples. The accuracy of identifying the state or condition by the trained algorithm may be calculated as the percentage of independent test samples (e.g., subjects known to have the state or condition or subjects with negative clinical test results for the state or condition) that are correctly identified or classified as having or not having the state or condition.

The trained algorithm may be configured to identify the state or condition with a positive predictive value (PPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The PPV of identifying the state or condition using the trained algorithm may be calculated as the percentage of datasets of ECG data and/or audio data identified or classified as having the state or condition that correspond to subjects that truly have the state or condition.

The trained algorithm may be configured to identify the state or condition with a negative predictive value (NPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The NPV of identifying the state or condition using the trained algorithm may be calculated as the percentage of datasets of ECG data and/or audio data identified or classified as not having the state or condition that correspond to subjects that truly do not have the state or condition.

The trained algorithm may be configured to identify the state or condition with a clinical sensitivity at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical sensitivity of identifying the state or condition using the trained algorithm may be calculated as the percentage of independent test samples associated with presence of the state or condition (e.g., subjects known to have the state or condition) that are correctly identified or classified as having the state or condition.

The trained algorithm may be configured to identify the state or condition with a clinical specificity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical specificity of identifying the state or condition using the trained algorithm may be calculated as the percentage of independent test samples associated with absence of the state or condition (e.g., subjects with negative clinical test results for the state or condition) that are correctly identified or classified as not having the state or condition.

The trained algorithm may be configured to identify the state or condition with an Area-Under-Curve (AUC) of at least about 0.50, at least about 0.55, at least about 0.60, at least about 0.65, at least about 0.70, at least about 0.75, at least about 0.80, at least about 0.81, at least about 0.82, at least about 0.83, at least about 0.84, at least about 0.85, at least about 0.86, at least about 0.87, at least about 0.88, at least about 0.89, at least about 0.90, at least about 0.91, at least about 0.92, at least about 0.93, at least about 0.94, at least about 0.95, at least about 0.96, at least about 0.97, at least about 0.98, at least about 0.99, or more. The AUC may be calculated as an integral of the Receiver Operating Characteristic (ROC) curve (e.g., the area under the ROC curve) associated with the trained algorithm in classifying datasets of ECG data and/or audio data as having or not having the state or condition.

The trained algorithm may be adjusted or tuned to improve one or more of the performance, accuracy, PPV, NPV, clinical sensitivity, clinical specificity, or AUC of identifying the state or condition. The trained algorithm may be adjusted or tuned by adjusting parameters of the trained algorithm (e.g., a set of cutoff values used to classify a dataset of ECG data and/or audio data as described elsewhere herein, or parameters or weights of a neural network). The trained algorithm may be adjusted or tuned continuously during the training process or after the training process has completed.

After the trained algorithm is initially trained, a subset of the inputs may be identified as most influential or most important to be included for making high-quality classifications. For example, a subset of the plurality of features (e.g., of the ECG data and/or audio data) may be identified as most influential or most important to be included for making high-quality classifications or identifications of the state or condition. The plurality of features or a subset thereof may be ranked based on classification metrics indicative of each feature's influence or importance toward making high-quality classifications or identifications of the state or condition. Such metrics may be used to reduce, in some cases significantly, the number of input variables (e.g., predictor variables) that may be used to train the trained algorithm to a desired performance level (e.g., based on a desired minimum accuracy, PPV, NPV, clinical sensitivity, clinical specificity, AUC, or a combination thereof). For example, if training the trained algorithm with a plurality comprising several dozen or hundreds of input variables in the trained algorithm results in an accuracy of classification of more than 99%, then training the trained algorithm instead with only a selected subset of no more than about 5, no more than about 10, no more than about 15, no more than about 20, no more than about 25, no more than about 30, no more than about 35, no more than about 40, no more than about 45, no more than about 50, or no more than about 100 such most influential or most important input variables among the plurality can yield decreased but still acceptable accuracy of classification (e.g., at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%). The subset may be selected by rank-ordering the entire plurality of input variables and selecting a predetermined number (e.g., no more than about 5, no more than about 10, no more than about 15, no more than about 20, no more than about 25, no more than about 30, no more than about 35, no more than about 40, no more than about 45, no more than about 50, or no more than about 100) of input variables with the best classification metrics.

The state or condition of the heart of the subject may be a type of a heart murmur, such as aortic stenosis (AS). Aortic stenosis may be a common disease which may be detected as a murmur on auscultation. A common method for detecting AS may be transthoracic echocardiography (TTE). In some cases, a referral from a healthcare provider who may have recognized an abnormality on auscultation may be needed for performing transthoracic echocardiography on subjects. However, in some cases, AS conditions may be hard to detect by physicians, particularly less experienced primary care physicians. For example, present AS conditions may be often not detected by less experienced primary care physicians. The methods of the present disclosure may facilitate the detection of AS at a sensitivity of at least about 80%, 85%, 90%, 95%, 98%, 99%, or more, and/or at a specificity of at least about 80%, 85%, 90%, 95%, 98%, 99%, or more. Furthermore, the methods may help quickly confirm suspected AS at a sensitivity of at least about 80%, 85%, 90%, 95%, or more, such as, for example, 97.2%, and a specificity of at least about 80%, 85%, 90%, 95%, or more, such as, for example, 86.4%. The state or condition of the subject may be determined using the trained algorithm. The trained algorithm may be trained for specific applications. For example, the trained algorithm may be trained for detection of aortic stenosis in which case it may be referred to as an Aortic Stenosis (AS) algorithm. The methods, devices and systems of the present disclosure may be used by healthcare providers during primary care visits. The methods of the present disclosure may facilitate the automatic detection of clinically significant AS, which may be further validated by transthoracic echocardiography (TTE). Phono- and electrocardiogram detection and analyses facilitated by the methods, devices and systems of the present disclosure may be used for detection of valvular and structural heart diseases.

The trained algorithm can also access a database to provide additional information that a healthcare provider may need to access or classify a state or condition of an organ of a subject. The database may comprise examples of ECG data and/or audio data of heartbeats associated with pre-existing certain states or conditions of the subject. The states or conditions can be related to a disease or healthy state, states or conditions comprising a biological or physiological condition, states or conditions comprising a diagnosis or determination, or unknown states. Further, the states or conditions can be related to an organ of the subject, such as, for example, a heart or a lung of the subject. The database may contain examples related to diagnoses or determinations of a low ejection fraction, congestive heart failure, arrhythmia, heart blockage, ischemia, infarction, pericarditis, hypertrophy, heart murmur, and more. For conditions like heart murmur, examples in the database may comprise diagnoses or determinations of a certain type of a heart murmur such as of a systolic murmur or a diastolic murmur. Moreover, examples in the database may comprise diagnoses or determinations of other conditions or states such as an aortic stenosis, a pulmonic stenosis, a mitral regurgitation, a tricuspid regurgitation, or a mitral valve prolapse, aortic regurgitation, a pulmonic regurgitation, a mitral stenosis, or a tricuspid stenosis, and more. The examples in the database can also include a healthcare provider's annotations on the determination of the state or condition of the subject, such as a diagnosis of a subject (e.g., a patient) in each case.

The trained algorithm may use the database to assist healthcare providers to identify or classify a state or condition of a subject based on the recorded audio data, ECG data, or a combination of audio and ECG data. The trained algorithm may compare the recorded audio data and ECG data associated with a condition or state separately or together in the database with recorded audio and/or ECG data using the disclosed sensor herein. For example, the algorithm may identify a number of examples from the database that are closest in terms of a plurality of features of ECG data and/or audio data to a recorded ECG or audio data of a subject using the sensor disclosed herein. Certain identified examples from the database may have similar intensity, pitch, or shape of recorded audio frequency data compared to recorded audio data by the monitoring device disclosed herein. Further, these identified examples from the database may have a similar average number of PR segments, ST segments, PR intervals, QRS intervals, ST intervals, or QT intervals of their ECG data compared to the ECG data recorded by the monitoring device disclosed herein. In some cases, the number of examples can be at least 1, 2, 3, 4, 5, 6, 7, 8, 9, 10, 11, 12, 13, 14, 15, 16, 17, 18, 19, 20, or more. In other cases, the number of examples can be 5. The number of examples is not meant to be limiting. The algorithm can search and locate several, such as 3, 4, 5, or 6 examples of recorded ECG and audio data associated with a certain type of heart murmur that contain the closest features compared to features associated with a ECG and/or audio data recorded by the disclosed sensor herein. This feature may be referred to as the k-nearest neighbor or n-nearest neighbor feature, where k or n may represent the number of examples identified from the saved database.

Subsequently, the algorithm can send a comparison of the closest examples from the database with the sensor generated ECG and/or audio data to a computing device or a cloud storage so a health care provider can have access to the comparison. The comparison may be sent to the computing device or cloud storage in real-time or substantially in real-time. This may facilitate decision-making regarding detecting or classifying a state or condition by taking into account relevant information about the subject and similarity of the recorded audio and ECG signals to examples from the database.

The trained algorithm provided in the present disclosure may provide healthcare providers with tools to more accurately detect states or conditions of subject, such as structural heart disease, during primary care visits.

Computing Device

The present disclosure provides computing devices which may receive data from sensors of varying modalities described elsewhere herein. For example, the computing device may receive ECG data or audio data. The computing device may comprise computer control systems that are programmed to implement methods of the disclosure.

The computing device may be configured to communicate with a monitoring device. The computing device may communicate with the monitoring device through a wireless communication interface. As an alternative, the computing device may communicate with the monitoring device through a physical (e.g., wired) communication interface. The computing device may communication with the monitoring device through a wide area network (WAN) which may include the Internet. The computing device may communicate with the monitoring device through a cellular network. The computing device may communicate with the monitoring device through an infrared communication link. The computing device may be configured to communicate with the monitoring device via a radio-frequency communication. For example, the radiofrequency communication may be Bluetooth, may be a standard wireless transmission protocol (e.g. WiFi), etc. The computing device may communicate with a server as part of a distributed computing system.

The computing device may be mobile. The computing device may be capable of movement from one place to another. The computing device may be a personal computer (e.g., portable PC, laptop PC), slate or tablet PC (e.g., Apple® iPad, Samsung® Galaxy Tab), telephone, Smart phone (e.g., Apple® iPhone, Android-enabled device, Blackberry®), or personal digital assistant.

The computing device may be separated from the monitoring device by a distance. For example, the distance may be within about 1 foot, 2 feet, 3 feet, 4 feet, 5 feet, 10 feet, 20 feet, 30 feet, 40 feet, 50 feet, 100 feet, 200 feet, 300 feet, 500 feet, 100 yards, 200 yards, 300 yards, 400 yards, 500 yards, 1000 yards, 1 mile, 5 miles, 10 miles, 100 miles, 500 miles, 1000 miles, 10,000 miles, 15,000 miles, or more between the monitoring device and the computing device.

In an example, the computing device may comprise a distributed computing system. In some examples, the distributed computing system may be in contact with a monitoring device and in connection with a mobile device. The computing device can be operatively coupled to a computer network ("network"). The network can be the Internet, an internet and/or extranet, or an intranet and/or extranet that is in communication with the Internet. The network in some cases is a telecommunication and/or data network. The network can include one or more computer servers, which can enable distributed computing, such as cloud computing. The network, in some cases with the aid of the computer system, can implement a peer-to-peer network, which may enable devices coupled to the computer system to behave as a client or a server.

The cloud computing network may enable remote monitoring of a subject. The cloud computing network may store subject data over time, such as ECG data and audio data. Subject data such as ECG data and audio data may be analyzed on a remote server via a cloud computing network. The remote server may perform calculations (such as analyzing data) with greater computational cost that a mobile device of a user.

The computing device, such as mobile device or a remote computing device, may include a user interface. The ECG data and audio data may be transmitted to the computing device for display on the user interface. The ECG data and audio data, or an output generated from such data, may be presented on the user interface over the time period in real time or substantially real time (e.g., a time delay of at most 1 millisecond with respect to when the ECG data and audio data was collected). In an example, the user interface is as a graphical user interface. Examples of UIs include, without limitation, a graphical user interface (GUI), web-based user interface, a mobile user interface, an app, etc. The user interface may comprise an app (e.g. a mobile application) as described elsewhere herein.

The user interface may comprise a web-based interface. For example, the web-based interface may be a secure web browser. The web-based interface may be a secure web page. The universal resource locator (URL) of the secure web page may be changed at the request of a user. Access data on the secure web page may be protected by a password. The URL may comprise a unique token which is generated for each session. The unique token may be given to a subject and/or a third party. The token may be associated with a subject. In some cases, the token may be associated with a session. The token may be associated with a third-party operator such as a physician. The token may comprise two-factor identification. The token may rotate with time. The token may be reissued or reassigned at any time. The secure web browser may be encrypted. The token may be associated with a cryptographic key. The token may be associated with biometric data. The token may be a single sign-on token.

In some cases, after transmitting and processing ECG data and audio data to the computing device, the processed ECG data and audio data indicating a state or condition of an organ of a subject can be transmitted back to the monitoring device. The monitoring device may be synced in real time or substantially real time with the computing device such as a mobile device. The transmission of processed ECG data and audio data from the computing device to the monitoring device is in real time or substantially real time. An output indicative of the determined state or condition of the subject may be provided on the monitoring device through an audio broadcasting so that a healthcare provider can hear the output in real time or substantially real time. Further, the output may include an intervention/treatment plan based on the determined state or condition of the subject, follow-up tests, preventive plans, and/or pharmaceuticals.

Figure 7:
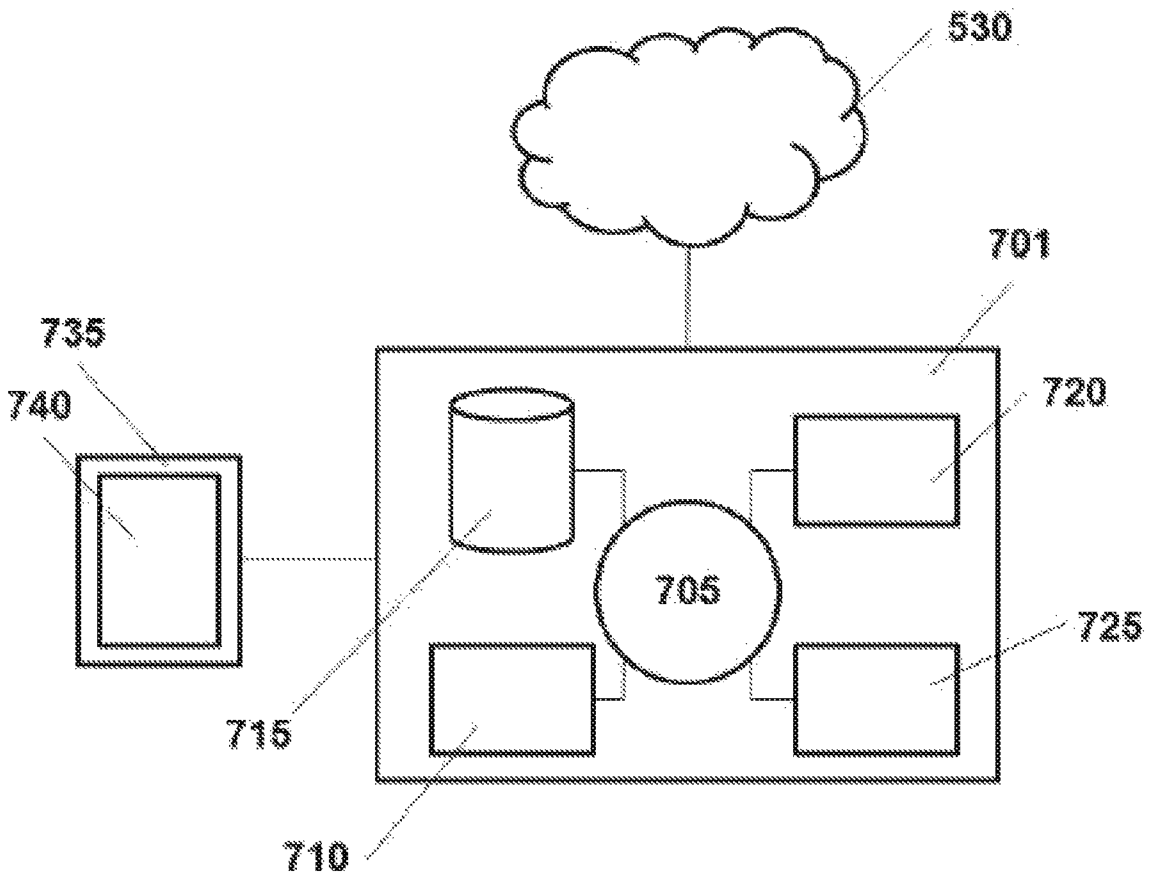
FIG. 7 shows a computer control system that is programmed or otherwise configured to implement methods provided herein.

FIG. 7 shows a computer system (also referred to herein as "computing device") 701 that is programmed or otherwise configured to receive ECG data and audio data from a monitoring device. The computer system 701 can regulate various aspects of the monitoring device of the present disclosure, such as, for example, processing the ECG and/or audio data, providing a an output indicative of a state or condition of a subject, provide a log of data over time. In some embodiments, the computer system 701 can be a computing device of a user or a computer system that is remotely located with respect to the monitoring device. The computing device can be a mobile computing device.

The computer system 701 includes a central processing unit (CPU, also "processor" and "computer processor" herein) 705, which can be a single core or multi core processor, or a plurality of processors for parallel processing. The computer system 701 also includes memory or memory location 710 (e.g., random-access memory, read-only memory, flash memory), electronic storage unit 715 (e.g., hard disk), communication interface 720 (e.g., network adapter) for communicating with one or more other systems, and peripheral devices 725, such as cache, other memory, data storage and/or electronic display adapters. The memory 710, storage unit 715, interface 720 and peripheral devices 725 are in communication with the CPU 705 through a communication bus (solid lines), such as a motherboard. The storage unit 715 can be a data storage unit (or data repository) for storing data. The computer system 701 can be operatively coupled to a computer network ("network") 530 with the aid of the communication interface 720. The network 530 can be the Internet, an internet and/or extranet, or an intranet and/or extranet that is in communication with the Internet. The network 530 in some cases is a telecommunication and/or data network. The network 530 can include one or more computer servers, which can enable distributed computing, such as cloud computing. The network 530, in some cases with the aid of the computer system 701, can implement a peer-to-peer network, which may enable devices coupled to the computer system 701 to behave as a client or a server. The computer system 701 can include or be in communication with an electronic display 735 that comprises a user interface (UI) 740 for providing, for example, an output indicative a state or condition of a user.

The CPU 705 can execute a sequence of machine-readable instructions, which can be embodied in a program or software. The instructions may be stored in a memory location, such as the memory 710. The instructions can be directed to the CPU 705, which can subsequently program or otherwise configure the CPU 705 to implement methods of the present disclosure. Examples of operations performed by the CPU 705 can include fetch, decode, execute, and write back.

The CPU 705 can be part of a circuit, such as an integrated circuit. One or more other components of the system 701 can be included in the circuit. In some cases, the circuit is an application specific integrated circuit (ASIC).

The computing device may store ECG data and audio data. The computing device may store ECG data and audio data on a storage unit. The storage unit 715 can store files, such as drivers, libraries and saved programs. The storage unit 715 can store user data, e.g., user preferences and user programs. The computer system 701 in some cases can include one or more additional data storage units that are external to the computer system 701, such as located on a remote server that is in communication with the computer system 701 through an intranet or the Internet.

The computer system 701 can communicate with one or more remote computer systems through the network 530. For instance, the computer system 701 can communicate with a monitoring device. In some embodiments, the computing device is a remote computer system. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. In some examples, the user can access the computer system 701 via the network 530.

Methods as described herein can be implemented by way of machine (e.g., computer processor) executable code stored on an electronic storage location of the computer system 701, such as, for example, on the memory 710 or electronic storage unit 715. The machine executable or machine readable code can be provided in the form of software. During use, the code can be executed by the processor 705. In some cases, the code can be retrieved from the storage unit 715 and stored on the memory 710 for ready access by the processor 705. In some situations, the electronic storage unit 715 can be precluded, and machine-executable instructions are stored on memory 710.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

Mobile Application

A mobile application is provided herein. A mobile application may provide the capability to initiate data collection, to stop data collection, to store data, to analyze data, and/or to communicate with a remote server or distributed computing network. In an example, the mobile application is installed on the mobile device of a user, such as a subject. In another example, the mobile application may be accessed by a web browser. The mobile application and the web-based interface may comprise substantially similar functionality.

In an example, a user may initiate a software application installed on a mobile device, such as a smart phone or a laptop. In some examples, the mobile application is downloaded by a user. The mobile application may comprise instructions such as machine readable code which may be executed by a processor, such as a central processing unit (CPU) or a micro-processing unit (MPU), of the present disclosure. When executed, the instructions may control the operation of the monitoring device. The mobile application may comprise a user interface, as described elsewhere herein. The user interface may provide guidance and instructions to the user via the user interface. For example the mobile application may provide visual displays on a display screen to illustrate proper placement of the monitoring device on the body of the subject.

The subject or another user may place the monitoring device on the subject's skin. The mobile device may provide guidance as to proper placement. The electrodes 110A and 110B may contact the skin of the subject. The sensor may measure electrical changes on the skin and or sound created from a patient organ.

The subject or another user may press the button 120 to initiate monitoring of the organ of the subject. Depression of the button may initiate simultaneous recording from multiple sensor modalities. The subject may hold sensor against their own chest, or another user may hold the sensor against the subject's chest. In some examples, the button remains depressed in order to take subject data. In other examples, a first press of the button starts collection and a second press of the button stops collection. In other examples, data collection may be stopped and started by a web-based interface.

After the button is depressed, patient data may be collected, such as ECG data and audio data. The collected data may be pre-processed on the monitoring device. For example, pre-processing may comprise amplification, filtering, compression, etc. of ECG and/or audio data. In some examples, the data may be stored locally for a time. The collected data, which may comprise pre-processed data, may then be transmitted to the computing device. The collected data may be transmitted to the computing device in real time. The collected data may be displayed on a user-interface in substantially real time. In examples where the computing device is a mobile device, the transmitted data may be accessed via a mobile application on a smart phone. In some examples, the transmitted data may also be accessible via a web-based interface.

The data collected from the organ of the subject may be published to other device of other users involved in the subject's care. For example, the ECG and audio data may be transmitted to a server via a network. The server may store subject data long term. The server may analyze data which may require greater processing power than may be possible on a mobile device such as a smart phone; however, in some embodiments, the data may be analyzed on the smart phone. In some examples, the server may be accessible by the computing device of a health care provider. The web-based interface may additionally be accessible by the computing device of a health care provider. The subject may use the monitoring device at home or in a remote location and may make data from the monitoring device available to a health care provider. The data available to a healthcare provider may enable remote diagnosis.

The data from the monitoring device may be available to third parties in real time or substantially real time. The data may be stored over time within the server. The data collected over multiple time periods may be stored within the server. The server may comprise a repository of historical data for later analysis.

The mobile application may provide feedback to the subject or to a user on the quality of the data. For example, a voice based audio feedback may alert the subject. The mobile application may use a speaker of the computing device. In another example, an on-screen alert may be visually displayed to alert the subject. The subject may be alerted during the course of acquisition of ECG and audio data. The monitoring device may execute a local application on the MPU to alert a user on the monitoring device. The computing device may execute a local application on the CPU to alert a user on the mobile application. The mobile application may display an alert and play audio feedback simultaneously.

The mobile application may additionally display instructions to improve data quality, such a instructing the subject or a user to change a position of the monitoring device. The mobile application may instruct the patient to stay still. The mobile application may alert a subject when data collection is complete. The mobile application may alert a subject when data quality is poor. The mobile application may display previous results. The mobile application may prompt a user to start a new data acquisition session. The mobile application may alert the subject when data has been reviewed by a health care provider. A health care provide may comprise a clinician, a physician, and/or another trained operator.

The mobile application may display a waveform of subject ECG data. The mobile application may display a waveform of subject audio data. The subject may simultaneously view both waveforms. The subject may view the waveforms in real time. A remote user may view one or both waveforms from a remote location in real or substantially real time. The user may be able to compare differences or similarities between the data. The user may be able to spot issues in collecting the data, such as waveform irregularities from excess movement, speaking, poor sensor contact, etc. The user may be able to monitor his or her own heartrate.

EXAMPLES

Figure 8:
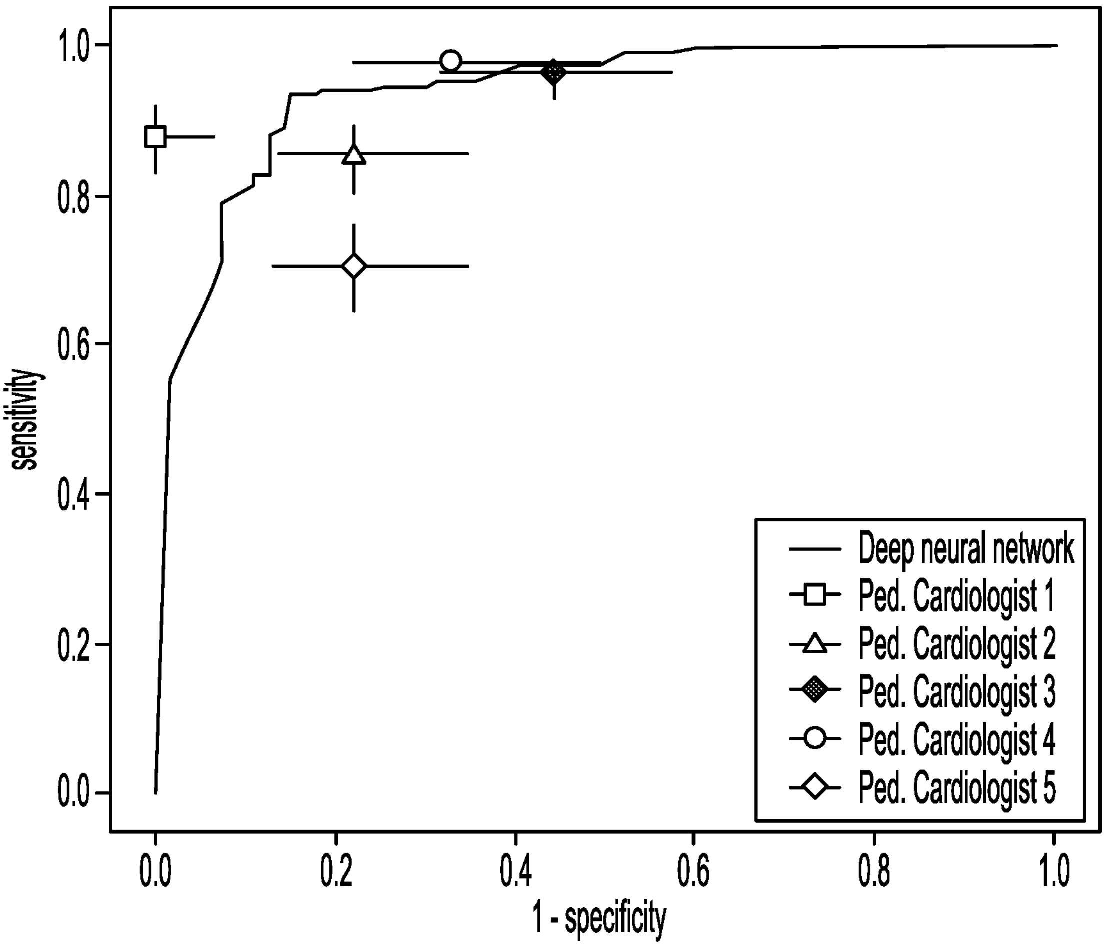
FIG. 8 shows a summary of algorithm performance versus five cardiologists.

Example 1: Performance of a Deep Neural Network Versus Cardiologists in Detecting Heart Murmurs FIG. 8 shows performance of five cardiologists and a receiver operating characteristic (ROC) curve for a deep neural network of the present disclosure. The data of the cardiologists are represented by 801, 802, 803, 804 and 805. The deep neural network data is represented by curve 806. A retrospective analysis of audio recordings from 54 patients collected at duPont Hospital for Children was performed using a monitoring device of the present disclosure. Only patients with echo-confirmed pathologic heart murmurs and normal heart sounds were included (n=42), while patients with innocent murmurs and other abnormal heart sounds were excluded. A deep neural network was trained on a separate murmur database and blinded to test data at the time of training. Recordings were analyzed by the network to predict probability of murmur presence, and this probability was thresholded to generate a receiver operating characteristic (ROC) curve.

Five pediatric cardiologists reported auscultation findings (pathologic murmur vs. no pathologic murmur) for each patient while blinded to echo findings and patient history. 95% confidence intervals for sensitivity and specificity relative to echocardiogram were computed via Wilson's method. As shown in FIG. 8, the ROC curve lies entirely below the 95% confidence interval (CI) for 1/5 clinicians, entirely above the 95% CI for 1/5 clinicians, and within the 95% CI for 3/5 clinicians.

Example 2: Performance of a Deep Neural Network Versus Echocardiography in Detecting Heart Murmurs FIG. 9 and FIG. 10 show a summary of results of a classification of a heart murmur database using gold standard echocardiography methods and a neural network disclosed herein. The Johns Hopkins University (JHU) heart murmur database is a collection of heart sound recordings curated by Professor W. Reid Thompson, M.D., at Johns Hopkins School of Medicine. This database includes annotated sounds collected at multiple positions with graded heart murmurs diagnoses confirmed via gold standard echocardiography. To ensure independence and prevent bias, all audio and annotation data are held by JHU and aggregate data on the performance of the algorithm are accessible by researchers. This database is used to provide independent confirmation of the algorithm's performance under use by a skilled user.

Overall, 2,534 of 3,180 files in the database were successfully analyzed (79.7%). For the primary outcome measure of distinguishing heart murmur recordings at the auscultation position at which the murmur is best heard (n=384 cases) from recordings with no murmur from auscultation at the left mid-sternal border (LMSB) position (n=122 controls), the algorithm performance is summarized in FIG. 9 and FIG. 10. Table 910 shows a summary of the results for all intensity grades of heart murmurs. Table 920 shows a summary of the results as a function of intensity grade of heart murmurs. The algorithm shows increased sensitivity for the highest intensity heart murmurs. Table 930 shows a summary of the results as a function of intensity grades of heart murmurs further including echo-confirmed pathologic murmurs. The algorithm shows increased sensitivity when echo data is included. FIG. 10 shows a summary of the results as a function of pathology.

Figure 14:
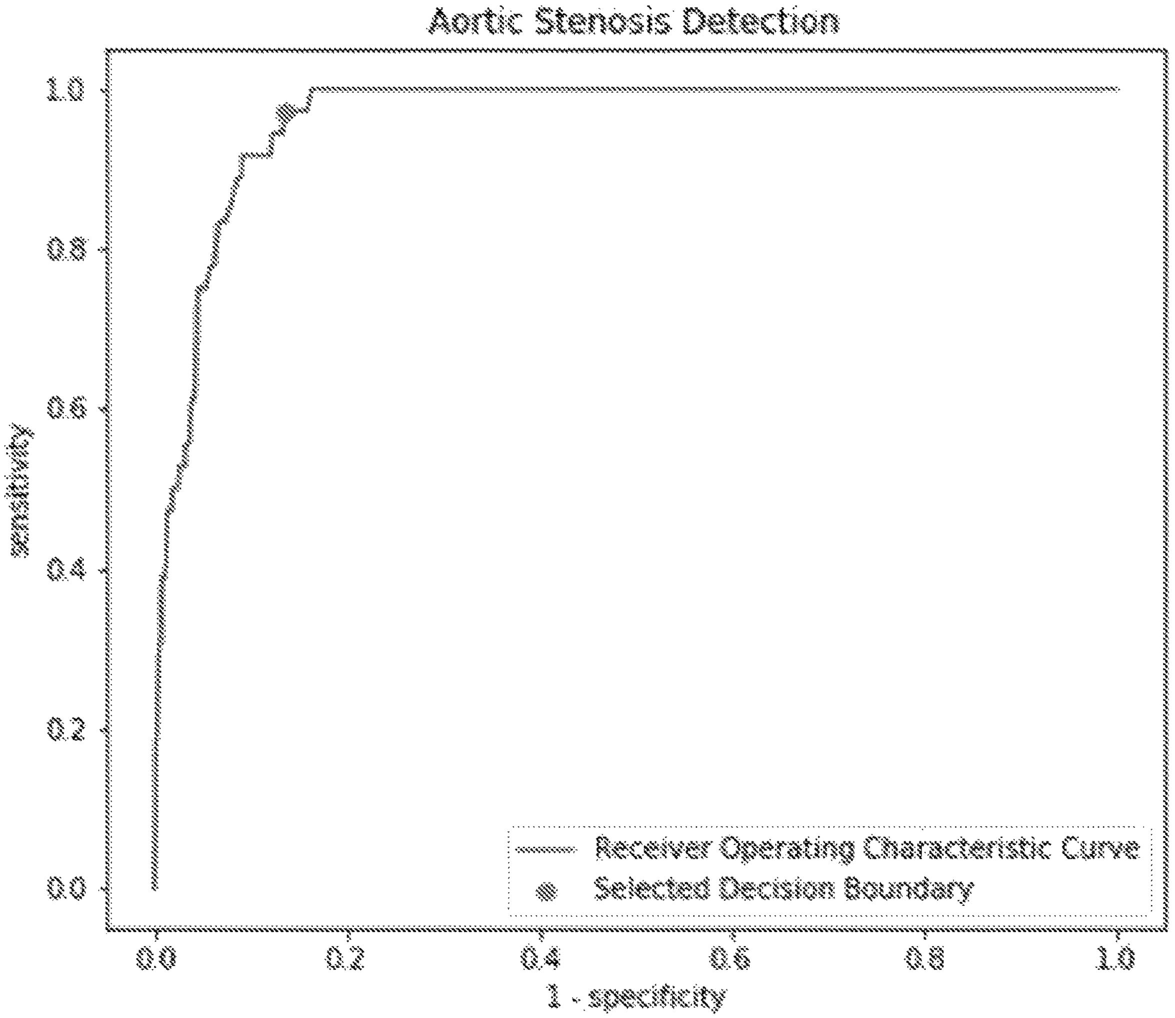
FIG. 14 shows a receiver-operating characteristic curve for detection of aortic stenosis (AS).

Example 3: Performance of a Deep Neural Network in Detecting Aortic Stenosis Consecutive patients undergoing transthoracic echocardiography (TTE) were prospectively enrolled to undergo phonocardiogram (PCG) recording by a method of the present disclosure. Recordings 15 seconds long were obtained at four standard auscultation positions (aortic, pulmonic, tricuspid, and mitral regions). A machine learning algorithm of the present disclosure assessed the presence or absence of murmur with dominant localization to the right upper sternal border indicating clinically significant aortic stenosis (AS), defined as moderate or greater on TTE. 161 patients were enrolled at the time of data analysis, yielding 639 recordings. FIG. 14 shows a receiver-operating characteristic (ROC) curve for detection of aortic stenosis (AS). 14 of these patients (8.7%) were found to have significant AS on TTE. The receiver-operating characteristic curve had an area of 0.964, yielding a sensitivity of 97.2% (95% CI, 84.7-99.5%) and a specificity of 86.4% (95% CI, 84.0-88.7%) for the detection of clinically significant AS.

Figure 15:
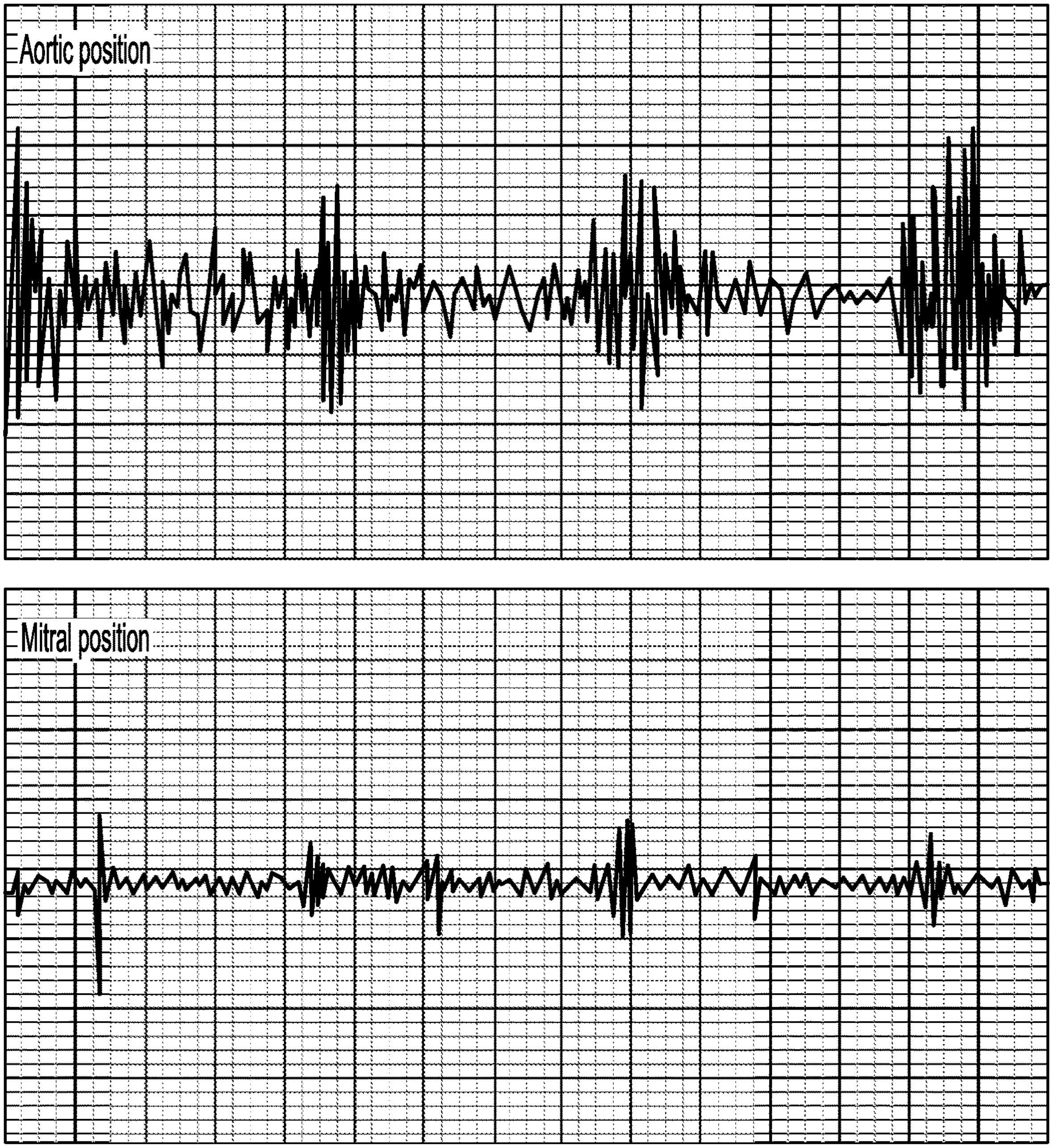
FIG. 15 shows a phonocardiogram (PCG) recording from a patient with significant aortic stenosis (AS) with intense signals observed in the aortic region.

FIG. 15 shows a phonocardiogram (PCG) recording from a patient with significant aortic stenosis (AS) with intense signals observed in the aortic region.

Figure 16:
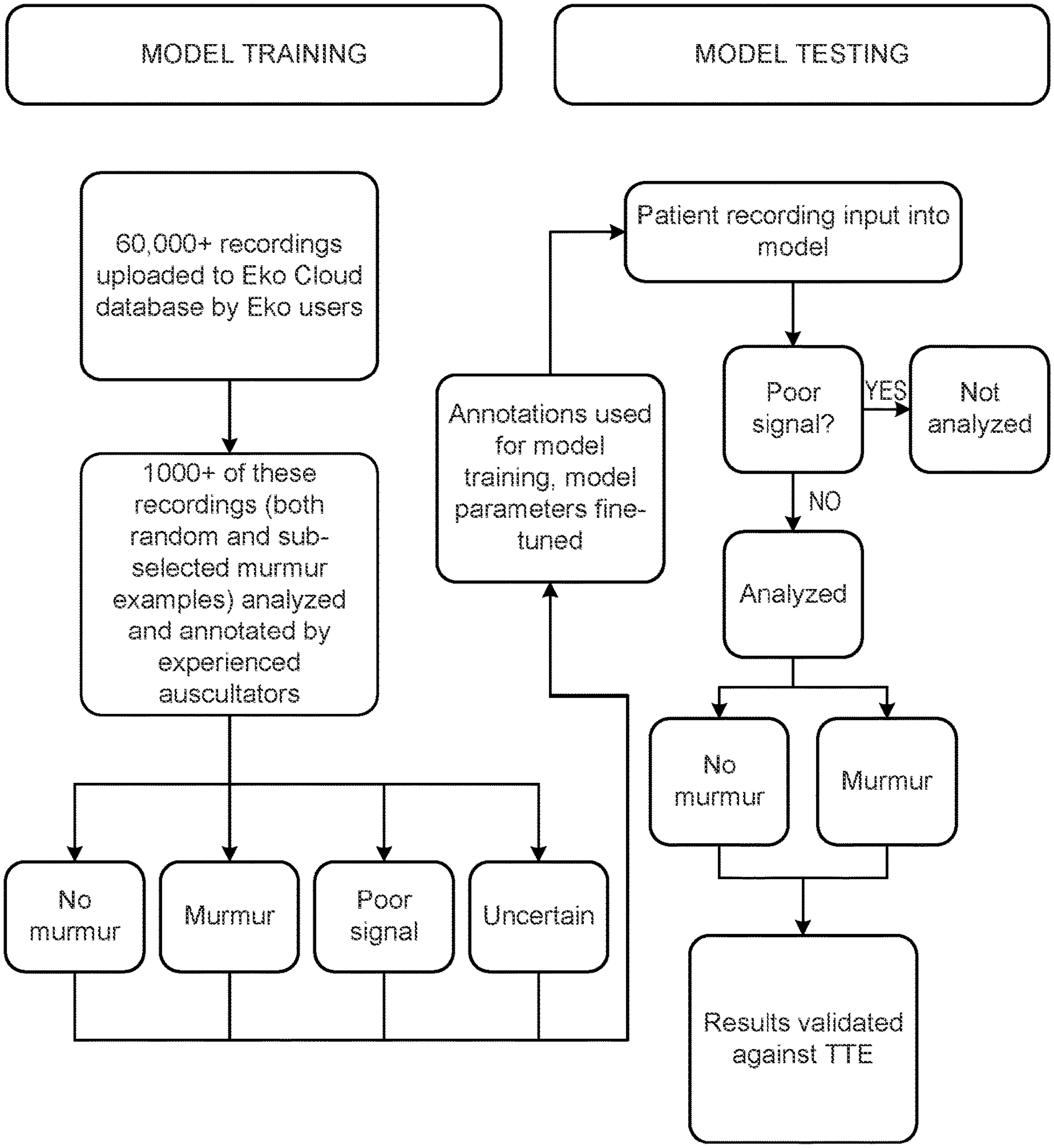
FIG. 16 shows an example flowchart for development and testing of a TensorFlow-based machine learning algorithm to detect aortic stenosis (AS).

FIG. 16 shows an example flowchart for development and testing of a TensorFlow-based machine learning algorithm to detect aortic stenosis (AS) using the methods of the present disclosure. The machine learning algorithm may be trained and tested. In example, more than 60,000 recordings were uploaded to the database of the computing device by users. More than 1000 of these recordings (both random and sub-selected murmur examples) were analyzed and annotated by experienced auscultators. Results were categorized in one of four categories: no murmur, murmur, poor signal, and unknown. The annotations were used for model training. Model parameters were fine tuned. The algorithm was further tested. Patient recordings were inputted into the model. If the signal was poor, the entry was not analyzed. If the signal was strong enough, the entry was analyzed. The data were categorized into one of two categories: no murmur and murmur. The results were further validated against TTE. As such, the model was trained and tested. PCG assessment using a method of the present disclosure was found to be fast and effective for detecting significant AS. The methods of the present disclosure may be validated in a primary care setting. Using the methods of the present disclosure for PCG assessment in a primary care setting may contribute to more appropriate referrals for an echocardiogram.

Example 4: Analysis Software for Evaluation of ECG Data and/or Audio Data

Using systems and methods of the present disclosure, an analysis software was developed to provide support to a physician in the evaluation of patients' heart audio data (e.g., from a digital stethoscope or other audio recorder) and ECG data. The software analyzes simultaneous ECG and heart audio data to detect the presence of suspected murmurs in the heart audio data. The software also detects the presence of atrial fibrillation and normal sinus rhythm from the ECG signal. In addition, it calculates certain cardiac time intervals such as heart rate, QRS duration, and EMAT. The analysis software is a cloud-based software application programming interface (API) that allows a user to upload synchronized ECG and heart audio or phonocardiogram (PCG) data for analysis. The software uses various methods to interpret the acquired signals, including signal processing and artificial neural networks. The API may be electronically interfaced and may perform analysis with data transferred from multiple mobile-based or computer-based applications.

The analysis software is configured to be used in conjunction with a system of the present disclosure (comprising ECG sensors and/or audio sensors), a companion mobile application (app) and a cloud-based infrastructure. The system may be configured to capture heart audio only, or both heart audio and ECG data (e.g., a single-lead ECG). The heart audio and ECG signals are transmitted to the mobile app using Bluetooth Low Energy. When a user makes a recording, a .WAV file is generated by the mobile app and transmitted to the cloud-based infrastructure, where the .WAV file is saved. This also triggers the analysis software API to perform analysis of the .WAV file. The analysis software is configured to output a JSON file with the algorithm results, which is passed down to the mobile device and displayed using the same mobile app.

Figure 17:
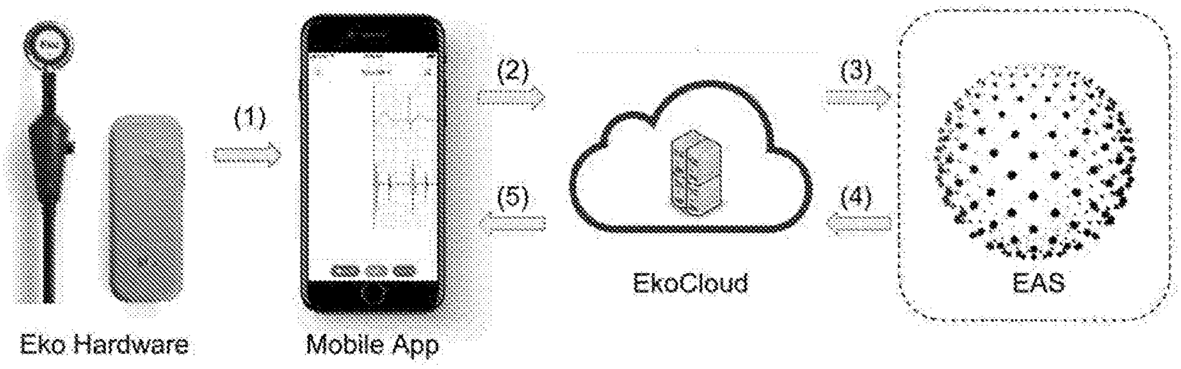
FIG. 17 shows an example of the interaction between different modules of a system, in accordance with some embodiments.

The interaction between different modules of the analysis software system is shown in FIG. 17. First, the hardware of the system may perform a data transfer to a mobile device via a Bluetooth Low Energy protocol. Second, a .WAV file is uploaded from the mobile device to a cloud-based infrastructure (e.g., EkoCloud). Third, data from the cloud-based infrastructure is sent for analysis using the electronic analysis software (EAS) API. Fourth, the analysis results are returned from the EAS to the cloud-based infrastructure as a JSON file. Fifth, the analysis results are sent from the cloud-based infrastructure to the mobile device, and displayed in a mobile app of the mobile device.

The analysis software system comprises the following algorithms of the present disclosure: (1) a rhythm detection algorithm that uses a neural network model to process ECG data to detect normal sinus rhythm and atrial fibrillation; (2) a murmur detection algorithm that uses a neural network model to process heart audio data to detect the presence of murmurs; (3) a Heart Rate algorithm comprising a signal processing algorithm that processes ECG data or heart audio data to calculate the heart rate of a subject, and provides an alert if the measured heart rate is indicative of an arrhythmia such as bradycardia or tachycardia; (4) a QRS duration algorithm comprising a signal processing algorithm that processes ECG data to measure the width of the QRS pulse; and (5) an EMAT interval algorithm comprising a signal processing algorithm that uses Q peak detection and S1 envelope detection to measure the Q-S1 interval, defined as electromechanical activation time or EMAT.

The analysis software comprises signal quality algorithms to assess the quality of the incoming ECG and PCG data. The model determines whether the recording is of sufficient signal quality to run the classifier algorithms. The signal quality indicators were trained based on noise annotations and/or poor signal annotations from the training dataset. Those annotations indicated whether the signal quality was too poor to reliably classify arrhythmias or heart murmurs (from ECG and heart audio data, respectively). That training effort resulted in signal quality analysis algorithms that determine whether the data is of sufficient quality and, if it is not, labels the recording as 'Poor Signal'. The signal quality algorithms are used prior to analysis by the algorithms described below.

The rhythm detection algorithm is configured to detect normal sinus rhythm and atrial fibrillation from ECG waveforms using a deep neural network model trained to classify ECGs into one of four categories: normal sinus rhythm, atrial fibrillation, unclassified, or poor signal. Following a determination of sufficient quality by the signal quality ECG algorithm, the rhythm detection classifier determines whether the signal shows presence of "Atrial Fibrillation" or can be classified as "Normal Sinus Rhythm" or represents other rhythms and is labeled as "Unclassified".

The murmur detection algorithm is configured to detect heart murmurs using a deep neural network model trained to classify heart sound recordings as containing a heart murmur or containing no audible murmur. Following a determination of sufficient quality by the signal quality PCG algorithm, the murmur detection classifier decides whether the signal shows presence of a "Murmur" or can be classified as "No Murmur".

The heart rate algorithm is configured to determine a heart rate using a signal processing algorithm that uses ECG or heart audio data. If ECG data are present and are determined to be of sufficient signal quality, then the median R-R interval from the detected QRS complexes is used to calculate the heart rate. If ECG are absent or of poor quality, the heart rate is computed from the PCG signal if it has good signal quality using an auto-correlation based analysis. If the signal quality of the PCG is also poor, then no heart rate value is presented. The ECG-based heart rate algorithm is a modified version of the classical Pan-Tompkins algorithm. In addition, EAS also generates a "Bradycardia" alert if the measured heart rate is below 50 BPM and a "Tachycardia" alert if the measured heart rate is above 100 BPM.

The EMAT algorithm comprises a signal processing algorithm configured to determine an EMAT. Following a determination of sufficient quality by the signal quality PCG and ECG algorithms, the EMAT algorithm uses Q peak detection on the ECG and S1 envelope detection on heart audio data to measure the Q-S1 interval, defined as electromechanical activation time or EMAT. EMAT interval calculation requires simultaneous recording of ECG and heart audio data. The reported % EMAT for an entire recording is reported as the median % EMAT of all beats in the signal.

Figure 18A:
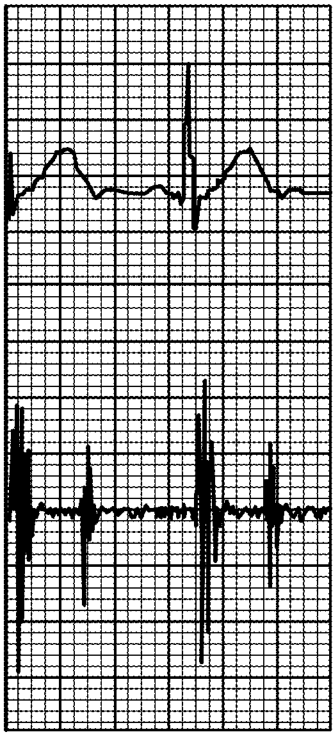
FIGS. 18A-18C show an example of a user interface of a mobile application, according to a disclosed embodiment, including a normal view (FIG. 18A), a view when a murmur is detected (FIG. 18B), and a view when an atrial fibrillation is detected (FIG. 18C).
Figure 18B:
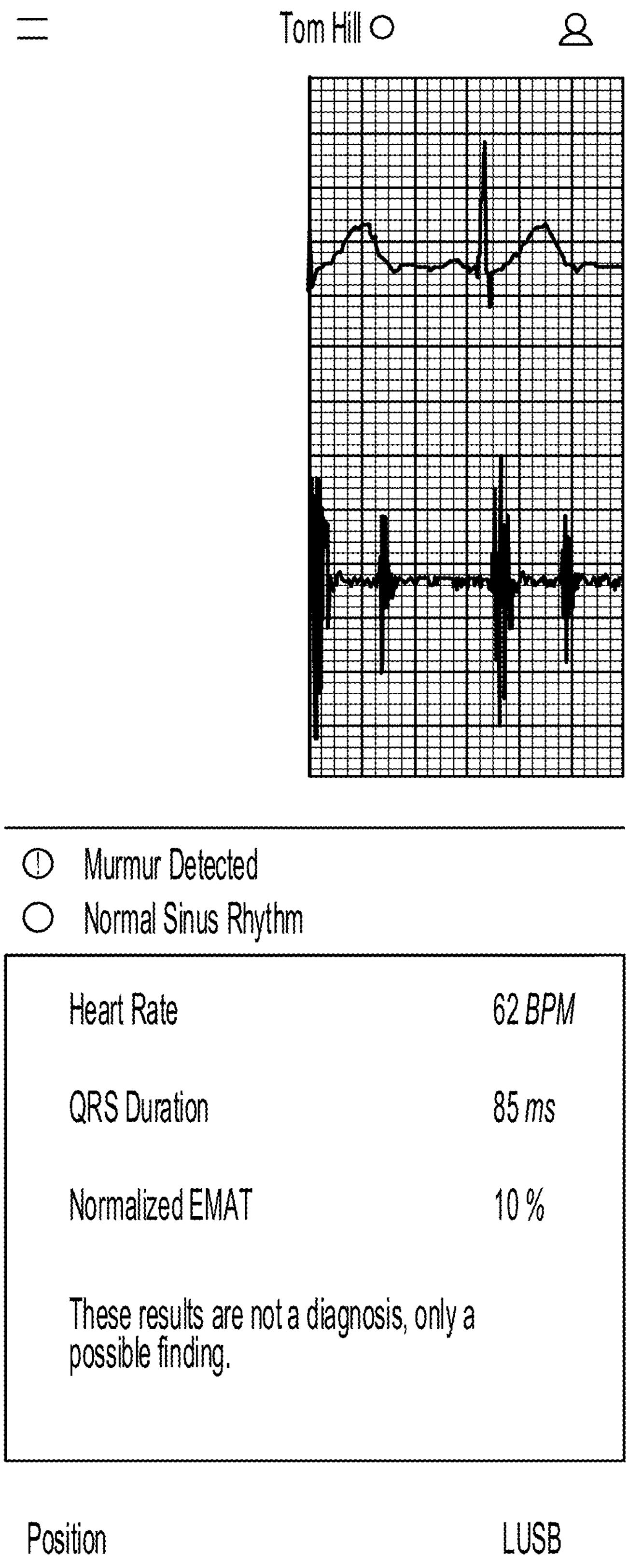
Figure 18C:
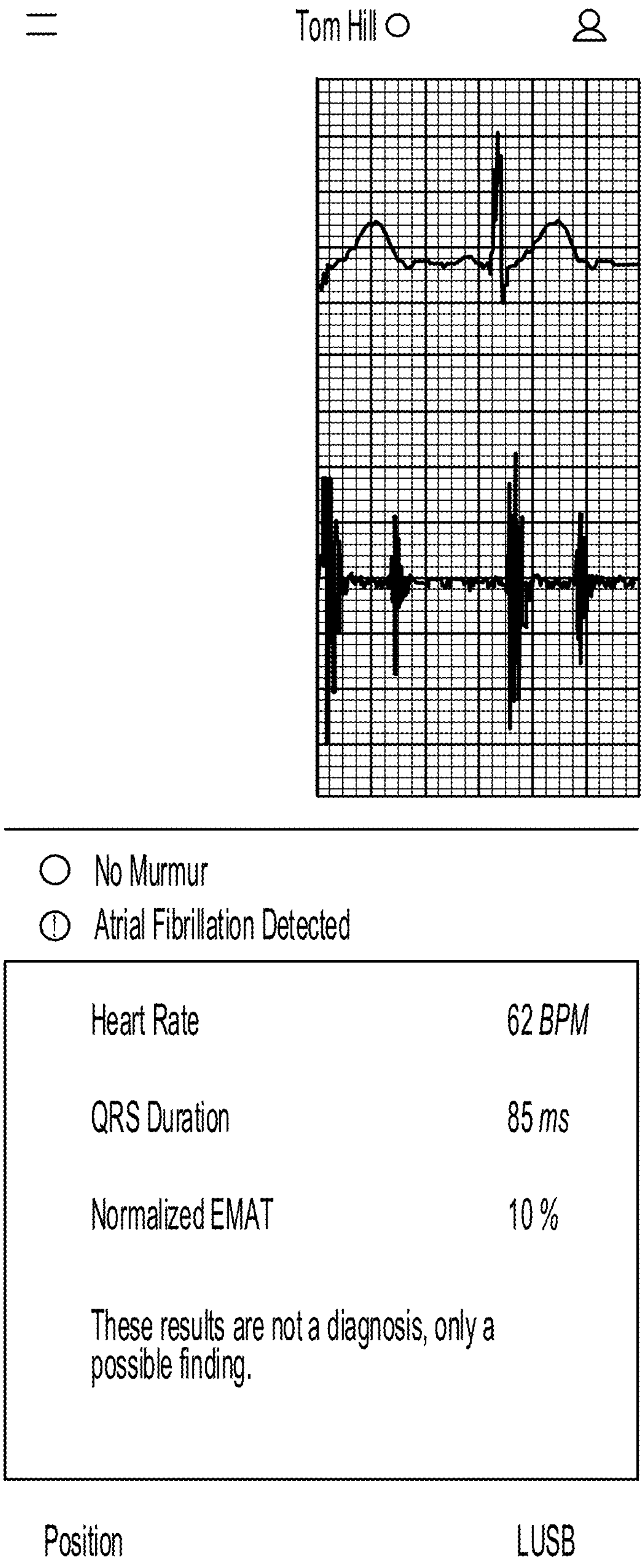

The analysis software may be configured to interface with a user interface software API. The analysis software may be configured to receive data from and provide results to other software applications through an API. The API result can be displayed by any mobile app or web interface to the clinician without any modifications to the terms or result. FIGS. 18A-18C show an example of a user interface of a mobile application, according to a disclosed embodiment, including a normal view (FIG. 18A), a view when a murmur is detected (FIG. 18B), and a view when an atrial fibrillation is detected (FIG. 18C). In addition to showing the ECG and heart sound waveforms, the mobile device is configured to display the result of the algorithms to clinicians, subjects, and other users in a simple, easy-to-read user interface.

The analysis software may be used to aid medical professionals in analyzing heart sounds and ECG data captured from hardware devices. The analysis software may also be used to support medical initiatives in digital collection and analysis of physiological data to provide more efficient healthcare. For example, the adoption of electronic health records may facilitate the continuity of health care, but must be augmented by other technologies to increase real-time access to patient data.

As a clinical evaluation method, auscultation may encounter challenges because of subjectivity, inability to quantify cardiovascular and pulmonary problems, and imprecision. For example, internal medicine and family practice trainees may accurately recognized only 20% of heart sounds. Heart audio analysis software can compensate for the limitations of acoustic stethoscopes. The analysis software is configured to detect the presence of murmurs in heart sounds, which then prompts the physician to conduct a more complete analysis of the detected murmur to determine whether it is innocent or pathologic. The analysis software's detection of the presence of murmurs are combined with clinician interpretations of heart sounds, of visualizations of heart sounds, and physician gestalt of clinical context to better determine appropriate follow-up. Although auscultation alone yields significant cardiac health information, synchronized ECGs can improve interpretation, as the data can provide insight into the heart rate and rhythm regularity. In addition, the analysis software is configured to perform atrial fibrillation detection using the single-lead ECG. The analysis software analyzes both ECG data and heart audio data to provide a comprehensive analysis of the electrical and mechanical function (as well as disorders) of the heart. For example, prolongation of the QRS duration can be indicative of a left ventricular dysfunction, such as left bundle branch block.

The analysis software algorithms were validated using retrospective analysis on a combination of publicly available (MIT-BIH Arrhythmia Database, MIT-BIH Arrhythmia Noise Stress Database, Physionet QT Database, and PhysioNet 2016 Database) and other databases. The recordings used for validation were distinct from data sets used to train the algorithm. As summarized in the below tables, each of the algorithms exhibited excellent performance in performing their respective detection tasks.

The algorithm's performance for rhythm detection is summarized in Tables 1A and 1B. These results show that the algorithm accurately identifies when the hardware gives a usable and good ECG signal. When a good signal is detected, the algorithm detects Atrial Fibrillation and Normal Sinus Rhythm with high accuracy (with a sensitivity and a specificity greater than the minimal clinical requirement of 90% sensitivity and 90% specificity).

TABLE 1A

| Rhythm detection on an ECG database (cases with good signal) | | |
|---|---|---|
| Performance | Prevalence (%) | Sensitivity (%) |
| Good Signal | 74.6% (95% CI: 71.3%-77.6%) | 85.7% (95% CI: 82.7%-88.2%) |

TABLE 1B

| Rhythm detection on an ECG database (cases with atrial fibrillation detection) | | |
|---|---|---|
| Performance | Sensitivity (%) | Specificity (%) |
| Atrial Fibrillation Detection | 100.0% (95% CI: 93.4%-100.0%) | 96.0% (95% CI: 93.5%-97.6%) |

The algorithm's performance for murmur detection is summarized in Tables 2A and 2B. These results show that the algorithm accurately identifies when the hardware gives a usable and good heart sound. Further, the algorithm detects the presence of murmur with high accuracy (with a sensitivity and a specificity greater than the minimal clinical requirement of 80% sensitivity and 80% specificity).

TABLE 2A

| Murmur detection on a heart sound database (cases with good signal) | | |
|---|---|---|
| Performance | Prevalence (%) | Sensitivity (%) |
| Good Signal | 87.8% (95% CI: 86.0%-89.4%) | 94.8% (95% CI: 93.5%-95.9%) |

TABLE 2B

| Murmur detection on a heart sound database (cases with murmur detection) | | |
|---|---|---|
| Performance | Sensitivity (%) | Specificity (%) |
| Murmur Detection | 87.6% (95% CI: 84.2%-90.5%) | 87.8% (95% CI: 85.3%-89.9%) |

The algorithm's performance for murmur detection is summarized in Tables 3A and 3B. These results show that the algorithm calculates heart rate with an error of less than the clinically acceptable limit of 5%. Further, the algorithm can accurately detect the presence of bradycardia and tachycardia (with a sensitivity and a specificity greater than the minimal clinical requirement of 90% sensitivity and 90% specificity), and generate alerts for a clinician accordingly.

TABLE 3A

| Heart rate detection on the MIT-BIH database (heart rate error) | |
|---|---|
| Performance | ECG |
| Heart Rate error (%) | 1.16% (95% CI: 0.96%-1.36%) |

TABLE 3B

| Heart rate detection on the MIT-BIH database (cases with bradycardia or tachycardia) | | |
|---|---|---|
| Performance | Sensitivity (%) | Specificity (%) |
| Bradycardia | 98.0% (95% CI: 94.3%-99.3%) | 97.6% (95% CI: 97.2%-98.1%) |
| Tachycardia | 94.6% (95% CI: 91.8%-96.5%) | 98.3% (95% CI: 97.9%-98.7%) |

The algorithm's performance for QRS duration detection is summarized in Table 4. These results show that the algorithm can calculate the QRS duration with an error of less than the clinically acceptable limit of 12%.

TABLE 4

| QRS duration detection on the PhysioNet QT database | | |
|---|---|---|
| Performance | Mean | Standard Dev |
| Absolute QRS error (ms) | 10.1 (95% CI: 8.55-11.6) | 7.64 (95% CI: 6.70-8.91) |
| Relative QRS error (%) | 9.20% (95% CI: 7.98%-10.4%) | 6.11% (95% CI: 5.35%-7.12%) |

The algorithm's performance for EMAT duration detection is summarized in Table 5. These results show that the algorithm can calculate the EMAT duration with an error of less than the clinically acceptable limit of 5% of the average R-R interval.

TABLE 5

| EMAT detection on an ECG database | |
|---|---|
| Performance | Actual |
| Absolute EMAT error (%) | 1.43% (95% CI: 1.15%-1.70%) |

Example 5: Performing Diabetic Flow Monitoring

In another example, a machine learning algorithm is developed to perform diabetic flow monitoring of a fluid status (e.g., blood). Patients with diabetes (e.g., type I or type II) may have a need to maintain a desired fluid volume, since their bodies may be unable to remove fluid as effectively as needed. However, conventional approaches of monitoring fluid volume or fluid flow may require invasive approaches involving venipuncture. Using systems and methods of the present disclosure, audio data of a fluid circulation of a subject may be collected and analyzed to determine a property of a fluid (e.g., blood) in the subject's body, such process may be used to replace the conventional venous access procedures, such as peripherally-inserted central catheters (PICC). This collection and analysis of audio data may be performed non-invasively with ECG sensors and/or audio sensors, without the use of venipuncture. The audio data of the fluid circulation may comprise audio data of blood flow across a fistula (e.g., a diabetic fistula) of the subject. The property of the fluid may comprise, for example, a fluid flow (e.g., a flow rate indicative of a volume of fluid per unit time), a fluid volume, a fluid blockage, or a combination thereof, of the subject. The property of the fluid may be characteristic of the fluid in a localized area of the subject's body, such as a location of vascular access or a diabetic fistula of the subject. One or more properties of the fluid, such as a fluid flow (e.g., a flow rate indicative of a volume of fluid per unit time), a fluid volume, or a fluid blockage, may be identified, predicted, calculated, estimated, or inferred based on one or more other properties of the fluid. For example, a flow volume (e.g., of blood) may be calculated or estimated based on a determined flow rate of the fluid.

Example 6: Collecting and Analyzing ECG Data and/or Audio Data from a Plurality of Different Locations or Parts of a Body Using systems and methods of the present disclosure, ECG data and/or audio data are collected from a plurality of different locations or parts of a body (e.g., organs or organ systems) of a subject, and then aggregated to provide an aggregate quantitative measure (e.g., a sum, an average, a median) of the plurality of different locations or parts of the body of the subject. The aggregate quantitative measure is then analyzed to determine a state or condition of the subject.

In some embodiments, the ECG data and/or audio data are collected from the plurality of different locations or parts of the body of the subject by a plurality of ECG sensors or leads (e.g., a 3-lead, 6-lead, or 12-lead ECG sensor) and/or audio sensors located at each of the plurality of different locations or parts of the body of the subject. In some embodiments, the ECG data and/or audio data are collected from the plurality of different locations or parts of the body of the subject by moving the ECG sensor and/or audio sensor to each of the plurality of different locations or parts of the body of the subject. The movement of the sensors may be performed by the subject or by a health provider (e.g., physician, nurse, or caretaker) of the subject.

In some embodiments, the ECG data comprise QT intervals, which may be analyzed to detect long QT intervals of the subject (which may correlate with or be indicative of an increased risk of heart failure of the subject). The QT interval measurements may be obtained by averaging ECG data acquired from a plurality of different locations of the heart of the subject. In some embodiments, a system or device of the present disclosure may comprise a sensor (e.g., an accelerometer) configured to detect if the device has been moved to different positions of the body (e.g., different positions of the heart) of the subject. The system or device may be configured to collect and analyze information of one or more movements or locations of the ECG sensor and/or the audio sensor corresponding to at least a portion of the ECG data and/or the audio data.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A system for determining a state or condition of a subject, comprising:

a communications interface configured to wirelessly communicate with a handheld monitoring device, said handheld monitoring device comprising an electrocardiogram (ECG) sensor and a single audio sensor for measuring ECG data and audio data, respectively, from said subject, said handheld monitoring device including a housing encasing said ECG sensor and said audio sensor, wherein said ECG data comprises single-lead ECG data; and a cloud computing network operatively coupled to said communications interface, wherein said cloud computing network is programmed to receive said ECG data and said audio data wirelessly from said communications interface in real-time, input said ECG data and said audio data into a neural network trained to output an ejection fraction of a heart of said subject in real-time based on said ECG data and said audio data, and provide an output indicative of said ejection fraction of said heart of said subject for display on a user interface in real-time.

2. The system of claim 1, wherein said handheld monitoring device is a mobile device.

3. The system of claim 1, wherein said ECG data and said audio data are transmitted in a common packet.

4. The system of claim 1, wherein said output indicative of said ejection fraction includes an output indicative of a presence or absence of a low ejection fraction of said heart of said subject.

5. The system of claim 4, wherein the presence or absence of the low ejection fraction of said heart of said subject is determined based on a percentage of said ejection fraction output by the neural network relative to a threshold percentage.

* * * * *